United States Patent [19]
Suga et al.

[11] Patent Number: 5,316,008
[45] Date of Patent: May 31, 1994

[54] MEASUREMENT OF ELECTROCARDIOGRAPHIC WAVE AND SPHYGMUS

[75] Inventors: Fusao Suga, Akishima; Narutoshi Minami, Musashino, both of Japan

[73] Assignee: Casio Computer Co., Ltd., Tokyo, Japan

[21] Appl. No.: 680,239

[22] Filed: Apr. 3, 1991

[30] Foreign Application Priority Data

| Apr. 6, 1990 | [JP] | Japan | 2-36623[U] |
| Nov. 30, 1990 | [JP] | Japan | 2-128045[U] |
| Nov. 30, 1990 | [JP] | Japan | 2-334923 |
| Nov. 30, 1990 | [JP] | Japan | 2-334924 |
| Dec. 21, 1990 | [JP] | Japan | 2-401398[U] |

[51] Int. Cl.$^5$ .............................. A61B 5/02
[52] U.S. Cl. .................. 128/700; 128/690; 128/696
[58] Field of Search ........... 128/700, 690, 695–696, 128/680–681

[56] References Cited

U.S. PATENT DOCUMENTS

| 3,132,643 | 5/1964 | Baum et al. | 128/672 |
| 3,318,303 | 5/1967 | Hammacher | 128/715 |
| 4,129,124 | 12/1978 | Thalmann | 128/690 |
| 4,129,125 | 12/1978 | Lester et al. | 128/702 |
| 4,869,262 | 9/1989 | Orr et al. | 128/672 |
| 4,898,180 | 2/1990 | Farrelly et al. | 128/681 |
| 4,907,596 | 3/1990 | Schmid et al. | 128/672 |
| 4,944,304 | 7/1990 | Nishing | 128/672 |

FOREIGN PATENT DOCUMENTS

| 2753165 | 1/1978 | Fed. Rep. of Germany | 128/690 |
| 3613889 | 10/1987 | Fed. Rep. of Germany | 128/690 |
| 8503211 | 10/1985 | United Kingdom | 128/672 |

OTHER PUBLICATIONS

"Watch Takes Pulse by Copying ECG", C. Cohen Electronics, Apr. 7, 1982 vol. 55, #7.

"This New Pulsar TM Monitors the Pulse (in addition to telling the time and date)" Houston Newspaper, Apr. 18, 1977.

Primary Examiner—Lee S. Cohen
Assistant Examiner—Jeffrey R. Jastrzab
Attorney, Agent, or Firm—Frishauf, Holtz, Goodman & Woodward

[57] ABSTRACT

A device is used for precisely measuring an electrocardiographic wave and sphygmus. The device displays a number of sphygmus or the highest and lowest blood pressure on the basis of measured data. In the device, it is judged if an electrocardiographic wave signal generated from an electrocardiographic wave detecting circuit and the sphygmus signal generated from a sphygmus detecting circuit have been output in a corresponding manner to each other. If not, or if one of the above signals has not been detected, either the gain of the electrocardiographic wave detecting circuit or the gain of the sphygmus detecting circuit is increased so as to allow a precise detection of the signal.

28 Claims, 18 Drawing Sheets

MEASUREMENT OF ELECTROCARDIOGRAPHIC WAVE AND SPHYGMUS

BACKGROUND OF THE INVENTION

1. Field of the Invention

The present invention relates to a device for measuring and/or displaying various data representation of heart motion such as sphygmogram data, sphygmus data, highest and lowest blood pressure data, blood flow rate data, electrocardiographic wave data and the like.

2. Description of Related Art

Devices for measuring and displaying sphygmus and highest and lowest blood pressure are available in the market and are used for keeping health. Among such known devices are involved pulsimeters for measuring sphygmus which, with use of LED and transistor arrangements, detect changes of hemoglobin in blood caused by pulsatory motion and senses electrocardiographic R-waves accompanied by heart motion, and haemadynamometers which, with use of an air pump, pressure tube and an acoustic or optical sensor, sense blood pressure by installing a cuff on a fingertip or arm of a subject.

Such devices, however, have drawbacks that are inconvenient in handling, requiring much time for a measurement, and are so large in size that it can not be carried in hand.

Under the circumstances, a device has been proposed which obtains blood pressure data without using an air pump. For example, U.S. Pat. No. 4,869,262 discloses a device which comprises a pulsimeter for sensing sphygmus in a fingertip of a subject and an R-wave detector for sensing electrocardiographic R-waves in the fingertip, and which performs a certain operation on data obtained by the pulsimeter and the R-wave detector to calculate blood pressure data.

Since the above device, however, senses sphygmus and electrocardiographic R-waves each in the fingertip, it has drawbacks that precise measurements of sphygmus and electrocardiographic R-waves can not be made in case that the finger is not set to a right position. Further, the measurements are easily influenced by external noises because the device senses very weak signals. Therefore, the resultant blood pressure is not always accurate one. As described above, as the device senses very weak signals, it includes an amplifier for amplifying the sensed weak signals. It is hard to set the gain of such amplifier for properly amplifying the sensed signals, because the sensed signals vary in level from subject to subject.

Conventional pulsimeter and haemadynamometer simply display sphygmus data and blood pressure data, respectively but they do not provide appropriate data for keeping or promoting health. Therefore, these meters are not used effectively by the subject for that purpose. To keep and promote health, the subject needs other data in addition to sphygmus data and blood pressure data, which teach what kind or how much of food he should take, and/or what exercises are suitable for him to keep health or to promote health.

SUMMARY OF THE INVENTION

The present invention has been made to overcome the drawbacks found in the prior art and has an object to provide a cardiac-data measuring device, which precisely senses sphygmus, electrocardiographic R-waves and the like.

Other object of the invention is to provide a device, which not only displays sphygmus, blood pressure and the like but also can be conveniently used by an exerciser who exercises to keep a normal blood pressure and sphygmus.

To achieve above objects, the present invention provides a cardiac-data measuring device, which comprises:

electrocardiographic wave detecting means for sensing an electrocardiographic wave within a human body;

first amplifying means for amplifying a signal supplied from said electrocardiographic wave detecting means to generate an electrocardiographic wave signal;

sphygmus detecting means for detecting sphygmus in a blood vessel;

second amplifying means for amplifying a signal supplied from said sphygmus detecting means to generate a sphygmus signal;

judging means for judging if both the electrocardiographic wave signal generated by said first amplifying means and the sphygmus signal generated by said second amplifying means have been output in a corresponding manner to each other; and gain control means for controlling either gain of said first amplifying means or gain of said second amplifying means when said judging means judges that said electrocardiographic signal and said sphygmus signal have not been output in a corresponding manner to each other.

The construction of the device according to the invention allows sphygmus and electrocardiographic R waves to be precisely sensed and further generates accurate cardiac data such as sphygmus data, blood pressure data, blood flow rate data and the like for promotion of health.

DESCRIPTION OF PREFERRED EMBODIMENTS

Now, embodiments of the present invention will be described in detail with reference to the accompanying drawings.

First Embodiment

Figure 1:
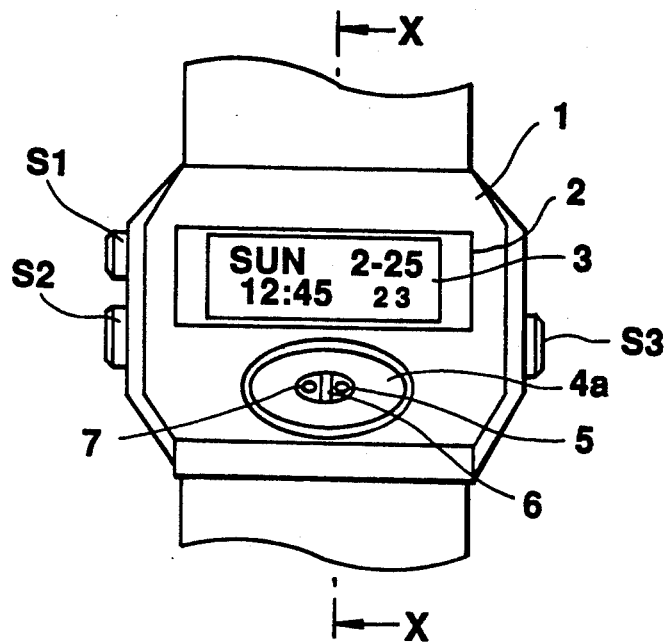
FIG. 1 is a view showing an external view of an electronic wrist watch employing the first embodiment of the present invention.

FIG. 1 is a view showing an external appearance of a wrist watch employing the first embodiment of the invention. In FIG. 1, a watch casing 1 is made from electrically non-conductive synthesis resin. On the front surface of the watch casing 1 are mounted a liquid crystal display section (hereafter, referred to as LCD) 3 of a rectangle, covered with a watch glass 2, at its slightly upper portion as viewed in FIG. 1 and an electrocardiographic-wave (hereafter, referred to as ECG wave) detecting electrode 4a of at its lower portion as viewed in FIG. 1.

Figure 2:
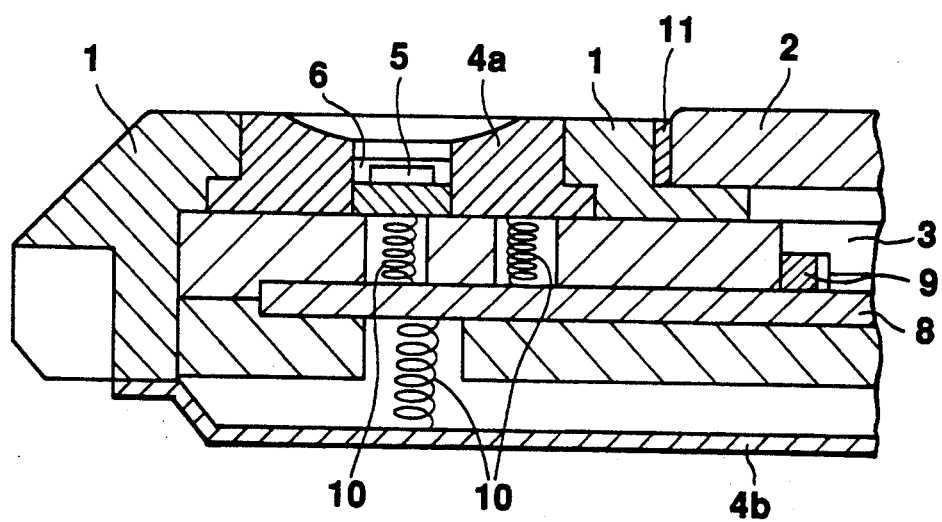
FIG. 2 is a partial cross-sectional view of the electronic wrist watch taken along the line X—X of FIG. 1.

The detecting electrode 4a of the electrocardiograph is formed with a recess in its front surface, where a light emission diode (hereafter, referred to as LED) 7 and a photo-transistor 5 separated by a partition 6 are embedded with their head portions exposed. The partition 6 prevents the light from LED 7 from being directly received by the photo transistor 6. On side walls of the watch casing 1 are mounted push button switches S1, S2 and S3 for changing display modes. FIG. 2 is a partial cross-sectional view of the electronic wrist watch taken along the line X—X running on the photo-transistor 5 of FIG. 1. As shown in FIG. 2, the watch glass 2 is fixed to the watch casing 1 with packing member 11. The bottom portion of the watch casing 1 is covered with a rear cover 4b, which is made of electrically conductive material, and serves as another ECG wave detecting electrode. Within the watch casing 1, a circuit board 8 involving an electronic circuit is installed as will be described later in more detail. LCD 3 is electrically connected to the circuit board 8 through an interconnector 9 and further the detecting electrode 4a and other electrode (the rear cover) 4b of the electrocardiograph, LED 7 and the photo-transistor 5 are electrically connected to the circuit board through conductive coil-spring members 10.

Figure 3:
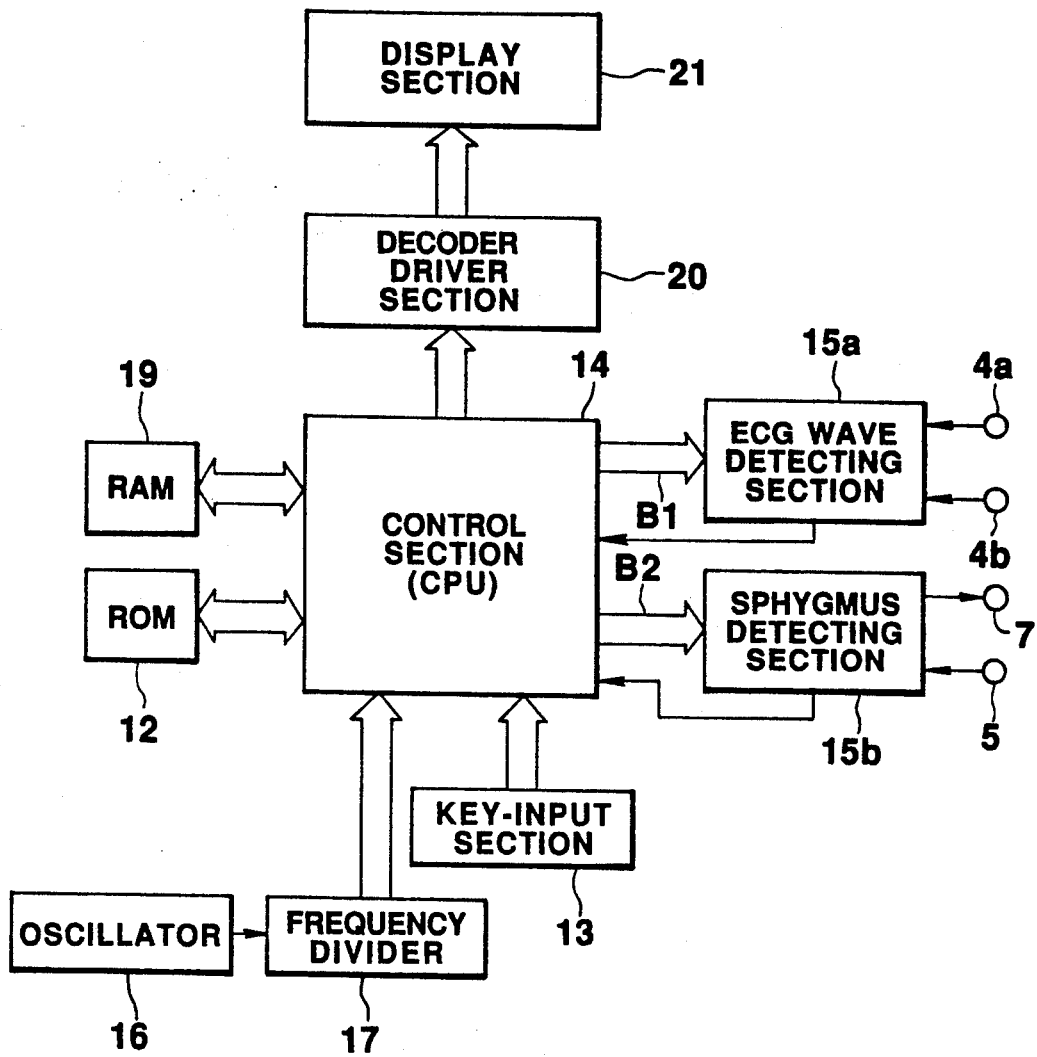
FIG. 3 is a circuit diagram installed within the electronic wrist watch.

FIG. 3 is a circuit diagram of an electronic circuit of the electronic wrist watch. A read only memory (hereafter, referred to as ROM) 12 is a fixed memory which stores a micro-program for controlling an operation of a system and numerical data used for various operations.

A key input section 13 including the switches S1, S2 and S3 shown in FIG. 1 supplies key-operation signals to a control section 14.

The control section 14 comprises a micro-processor or a central processing unit (hereafter, referred to as CPU), which controls the operation of the whole system on the basis of the micro-program stored in ROM 12. The control section 14 supplies an operation signal to an ECG wave detecting section 15a through a bus line B1 to start up the same and also supplies another operation signal to a sphygmus detecting section 15b through a bus line B2 to start up the same, when the control section 14 receives from the key-input section 13 a key-operation signal which instructs a display of sphygmus. After both the detecting sections 15a, 15b have started up, the control section 14 supplies them with a gain control signal to control respective gain control sections. Further, the control section 14 performs a time-counting process on the basis of a time-count timing signal supplied from a frequency divider 17, which will be described later.

The ECG wave detecting section 15a is connected with the ECG wave detecting electrodes 4a and 4b of FIG. 1. A user or a subject uses the ECG wave detecting section 15a to detect electrocardiographic R waves with his right fingertip being in contact with the ECG wave detecting electrode 4a while his left wrist being in contact with the ECG wave detecting electrode 4b. Then the ECG wave detecting section 15a outputs the ECG wave signal to the control section 14. The sphygmus detecting section 15b is connected with the photo transistor 5 and LED 7 of FIG. 1, and senses pulsating flow of blood in a blood vessel in his right fingertip, detecting sphygmus and supplies the sphygmus data to the control section 14. The property of hemoglobin in blood that sensitively absorbs light allows detection of sphygmus. That is, light emitted from LED 7 is absorbed by hemoglobin in blood while the light penetrates into the fingertip and reflected therefrom and the absorbed rate of the light is proportional to quantity of blood flow in the fingertip. When pulsating flow of blood passes in a blood vessel, quantity of blood flow increases, absorbing much of the light emitted from LED 7. As a result, the light reflected from the fingertip decreases and the light received by the photo transistor 5 changes in response to sphygmus. The variations in the light received by the photo transistor 5 are converted into an electric signal, which is transferred to the control section 14 as the sphygmus signal.

The control section 14 calculates a number of sphygmus per minute from the ECG wave signal supplied from the ECG wave detecting section 15a and the sphygmus signal supplied from the sphygmus detecting section 15b and supplies the sphygmus-number data to a decoder driver section 20.

The decoder driver section 20 decodes a display driving signal on the basis of the sphygmus-number data supplied from the control section 14 and supplies the display driving signal to a display section 21. The display section 21 comprises LCD 3 of FIG. 1 and makes a certain display on LCD 3 on the basis of the display driving signal supplied from the decoder driver section 20.

An oscillator 16 generates and supplies a clock signal of a predetermined period to the frequency divider 17. The frequency divider 17 comprises a frequency-dividing circuit and a timing-signal generator (both, not shown), and supplies the control section 14 with the time-count timing signal and a timing signal for sequentially controlling operations of various sections.

Figure 4:
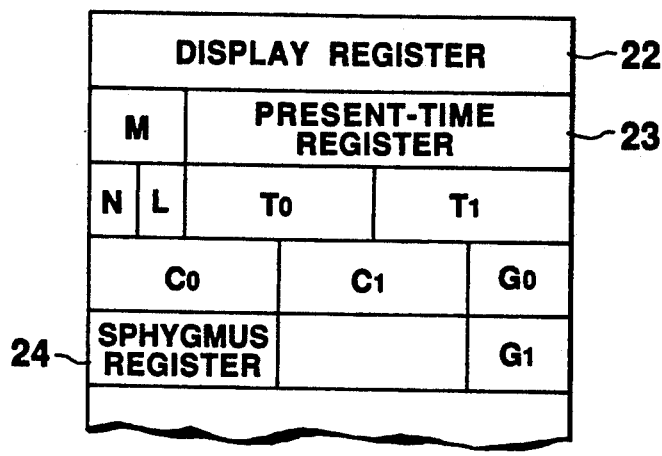
FIG. 4 is a view showing an internal construction of RAM of FIG. 3.

RAM 19 is a random access memory, which has a construction as shown in FIG. 4. In FIG. 4, a display register 22 stores display data to be displayed on LCD 3 of the display section 21.

A present-time register 23 stores present time counted by the control section 14 on the basis of the signal supplied from the frequency divider 17.

A register M is a flag register corresponding to the display mode. The flag register M stores alternatively "0" (a watch mode) or "1" (a sphygmus detection mode) in response to an operation of the switch S1.

A register N is a flag register, which is reset to "0" at the start of measurement of ECG wave and is set to "1" at the first detection of ECG wave.

A register L is a flag register, which is reset to "0" at the start of measurement of sphygmus and is set to "1" at the first detection of sphygmus after detection of ECG wave.

A register T0 is a timer, which counts time interval between the time when an ECG wave was detected and the time when the following ECG wave is detected.

A register T1 is a timer, which counts time interval between the time when a sphygmus was detected and the time when the following sphygmus is detected.

A register C0 stores time data counted by the register T0.

A register C1 stores time data counted by the register T1.

A register G0 stores gain data of ECG wave signal.

A register G1 stores gain data of sphygmus data.

A sphygmus register 24 is a register for storing sphygmus data (number of sphygmus per minute) counted by the control section 14.

Figure 5A:
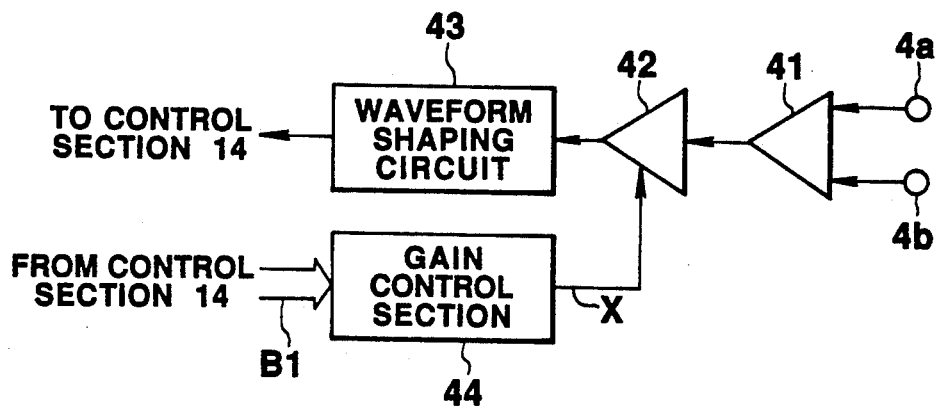
FIG. 5A and 5 are views showing a circuit of an electrocardiogram detecting section and a circuit of a sphygmus detecting section, respectively.

FIG. 5A is a circuit diagram of the ECG wave detecting section 15a of FIG. 3. In FIG. 5A, a signal from the ECG wave detecting electrodes 4a, 4b of the ECG wave detecting section 15a is supplied to a differential amplifier 41, which detects ECG potential signal from a potential at the ECG detecting electrodes 4a, 4b and supplies the detected ECG potential signal to a variable-gain amplifier 42. The variable-gain amplifier 42 amplifies the ECG potential signal supplied from the differential amplifier 41 at a gain decided by a gain control signal X. The gain control signal X is supplied from a gain control section 44, which develops the gain control signal X on the basis of a value delivered from the register G0 in RAM 19 through the bus line B1. The output of the variable-gain amplifier 42 is supplied to a waveform shaping circuit 43. The waveform shaping circuit 43 converts the analog signal supplied from the variable-gain amplifier into a digital signal consisting of a pulse train having a constant amplitude, and supplies the digital signal to the control section 14.

Figure 5B:
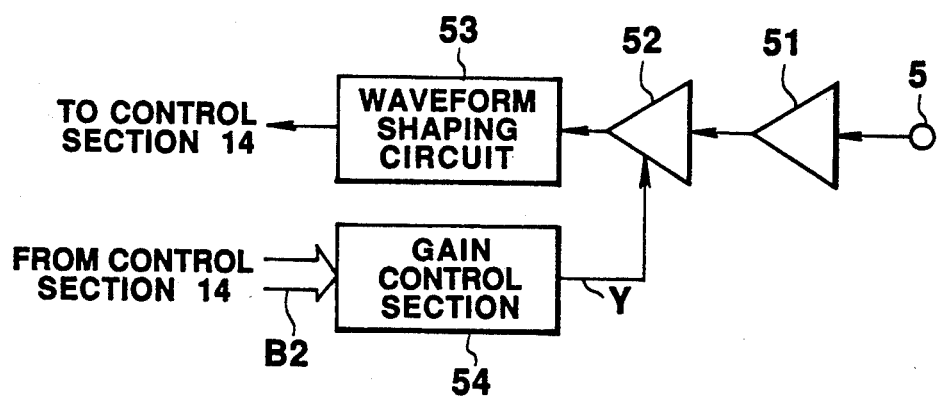

FIG. 5B is a circuit diagram showing the sphygmus detecting section 15b of FIG. 3 for processing sphygmus signal in a similar manner to the ECG wave detecting section 15a. As shown in FIG. 5B, the sphygmus detecting section 15b comprises a differential amplifier 51, a variable-gain amplifier 52, a waveform shaping circuit 53 and a gain control section 54. The gain control section 54 is arranged to develop a gain control signal Y on the basis of a value delivered from the register G1 in RAM 19 through the bus line B2, and supplies the gain control signal Y to the variable-gain amplifier 52.

Figure 7:
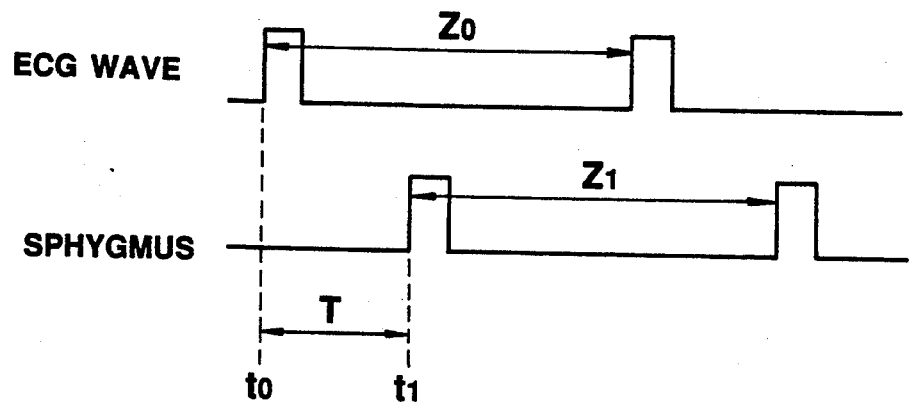
FIG. 7 is a timing chart showing a relative relationship in time between the electrocardiogram and the sphygmus.

In the present embodiment, both the detection of ECG waves and the detection of changes in blood flow in a fingertip are used for detection of sphygmus. Sphygmus and ECG wave can not always be detected precisely either by detecting ECG wave or by detecting changes of blood flow in a fingertip. Therefore, in the present embodiment, to detect precise sphygmus, ECG wave and changes of blood flow sphygmus are detected at the same time, and the results of detections are compared with each other to judge if they are closely related. A relationship in time between the ECG wave and sphygmus is shown in FIG. 7. Waveforms of the ECG wave and sphygmus are shown in FIG. 7.

As shown in FIG. 7, since ECG wave is an electric signal which flows in a human body in a moment, the ECG wave reaches to skin (both hands) of the human body at the almost same time t0 as the time when pulsatory motion of the heart generates the ECG wave, and is detected by the ECG wave detecting section 15a while, since sphygmus meets resistance due to a form and a quality of blood vessel, sphygmus reaches to skin (fingertip) of the human body at a time t1 or reaches late by a time lapse T from the time t0, and is detected by the sphygmus detecting section 15b. Following the ECG wave at the time t0, the next ECG wave is detected after a time lapse Z0 from the time t0 while the next sphygmus corresponding to the above next ECG wave is detected after a time lapse Z1 from the time t1. The time intervals Z0, Z1 between pulses are substantially equivalent.

Now, a sphygmus detecting process will be described in detail referring to the flowchart of FIG. 6. The control section (CPU) 14 starts the sphygmus detecting process, when the switch S1 of FIG. 1 has been operated, setting a flag of "1" to the register M of RAM 19 shown in FIG. 4 or when a sphygmus detecting mode has been set. In the meantime, the registers G0, G1 of RAM 19 for storing gain data hold a predetermined values, respectively, for instance, at the time when a power supply is turned on.

Figure 6:
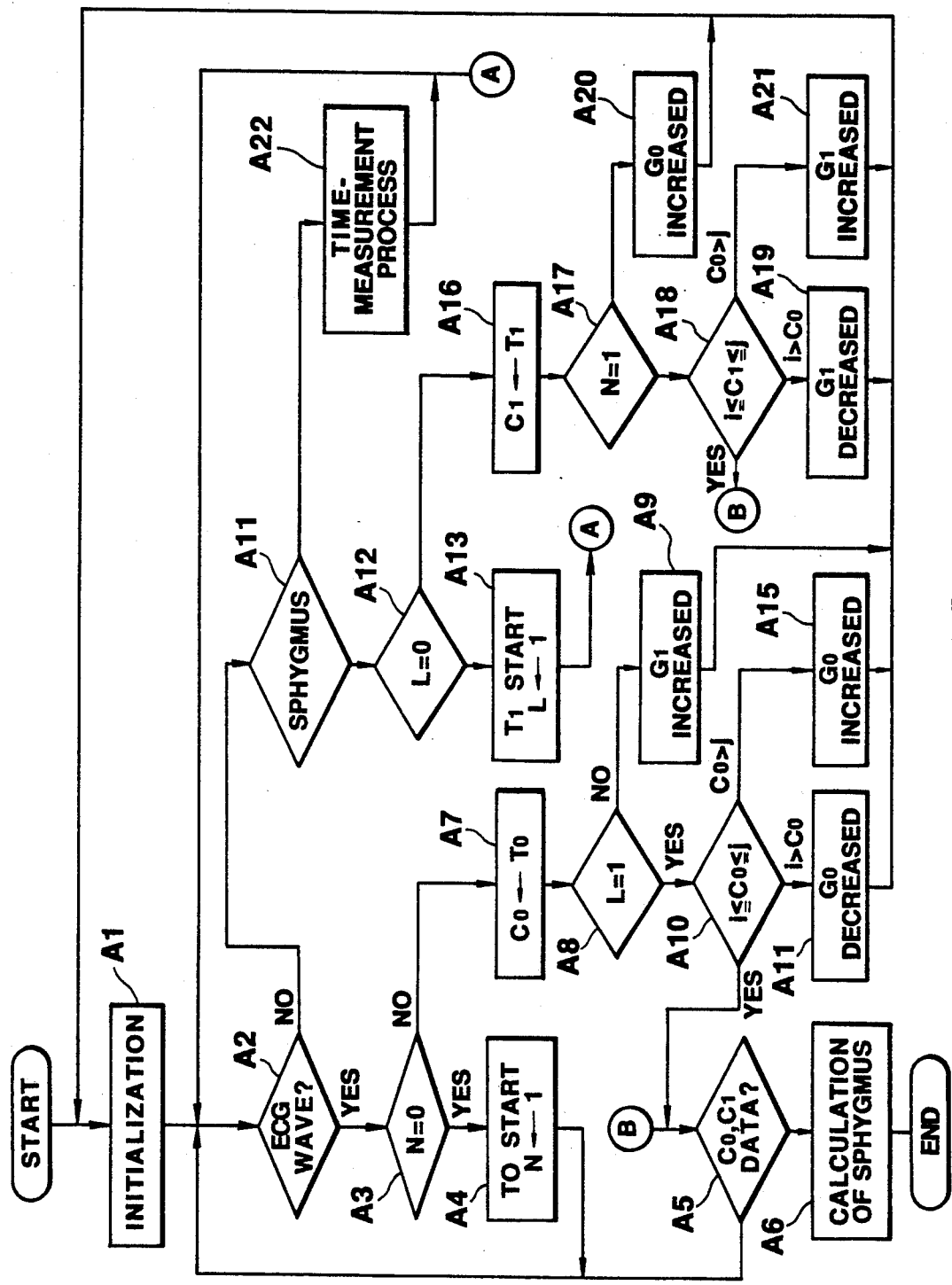
FIG. 6 is a flowchart showing an operation of the electronic wrist watch.

At step A1 in FIG. 6, the flag registers N, L, the registers Co, C1 for storing time data and timers T0, T1 are initialized. The operation goes to step A2, where it is judged if an ECG pulse signal has been detected by the ECG wave detecting section 15a.

When the control section 14 judges that the ECG pulse signal has been detected, the operation is advanced to step A3, where it is judged if the flag register N still holds a flag "0". A flag "0" held in the flag register N indicates that ECG wave had not been detected since the very start of the sphygmus detecting process and the first ECG wave has been detected. Therefore, at step A4, for measurement of a time interval to the detection of the following ECG wave or for measurement of the time interval Z0 shown in FIG. 7, the timer T0 is caused to start its time counting operation and a flag "1" is set to the register N to indicate that the first ECG wave has been detected. Then, the operation returns to step A2.

When it is judged again at step A2 that ECG wave has been detected, the operation goes to step A7 this time since it is judged at step A3 that a flag "1" has been set to the register N. At step A7, time data (time interval Z0 of FIG. 7) counted by the timer T0 is transferred to the register C0. The operation goes to step A8, where it is judged if the register L has been set to a flag "1". If not, or if the register L has been set to a flag "0", it is judged that a sphygmus wave signal has not been detected during the measurement of two ECG waves, that is, a flag "0" held in the register L indicates that no sphygmus has been detected at the time t1 of FIG. 7. Then, the operation goes to step A9, where gain data in the register G1 is increased by a predetermined degree and the operation returns to step A1.

In case that no sphygmus has been detected after ECG waves were detected, gain data in the register G1 is increased in the sphygmus detecting process and the gain control section 54 of the sphygmus detecting section 15b is controlled by the increased gain control signal Y to increase the gain of the variable-gain amplifier 52. Then, the sphygmus detecting process is performed again to detect a sphygmus pulse that was not detected during the time interval Z0.

When it is judged at step A8 that the register L holds a flag "1", this flag "1" indicates that the first sphygmus pulse corresponding to the first detected ECG pulse has been detected. Then the operation goes to step A10, where it is judged if "i≦C0≦j" is true. That is, it is judged if the time data (the time interval Z0 of FIG. 7) transferred to the register C0 falls in the range defined by constants i and j, where a constant i is 300 mS. (0.3 sec.) and a constant j is 2 sec.

When it is judged at step A10 that i>C0 is true, the pulse waveform detected by the ECG wave detecting section 15a has a repeat interval of not more than 300 mS. (0.3 sec.). This is the case that external noises other than ECG wave to be picked up were picked up. In this case, the operation returns to step A11, where gain data in the register G0 is reduced by a predetermined degree, and then the operation returns to step A1.

In the following ECG wave detecting process, the gain control signal X decreases the gain of the variable-gain amplifier 42 by a predetermined degree, because the gain data was reduced by a predetermined degree. As a result, no weak signals of no importance are picked up.

When it is judged at step A10 that C0>j, this is the case that the pulse waveform detected by the ECG wave detecting section 15a has a repeat interval of more than 2 sec. This repeat interval of the detected pulse waveform is longer than that of ECG wave, which means that no ECG wave to be detected was not detected. Then, the operation goes to step A15, where the gain data of the register G0 is increased by a predetermined degree, and the operation instantly returns to step A1.

In the ECG wave detecting process, the gain control signal X of the register G0 increases the gain of the variable-gain amplifier 42 by a predetermined degree, because the gain data X was reduced by a predetermined degree. As a result, ECG wave, which failed to be detected, is picked up.

When it is judged at step A10 that i≦C0≦j, this is the case that a normal ECG wave has been detected. Then, the operation goes to step A5, where it is judged if time data has been transferred to the register C1. If not, the operation goes back to step A2.

As described above, when, after ECG wave has been detected, no sphygmus pulse corresponding to the ECG pulse is detected, the gain of the variable-gain amplifier 52 is increased for detecting sphygmus pulse and the ECG pulse detecting process is repeated. When the sphygmus pulse corresponding to the ECG pulse has been detected, the ECG wave detecting process is performed to detect the following ECG pulse and it is judged if the detected pulse is ECG pulse. Meanwhile, the counted time interval between sphygmus pulses is transferred and stored in the register C0.

When it is judged at step A2 that no ECG pulse has been detected, the operation goes to step A11, where it is judged if the sphygmus detecting section 15b has detected a sphygmus wave signal (sphygmus pulse shown in FIG. 7).

When a sphygmus wave signal has been detected, the operation goes to step A12, where it is judged if a flag "0" has been set to the register L. If the flag "0" has been set to the register L, this is the case that sphygmus had not been detected since the very beginning of the process, that is, the detected sphygmus wave signal is the first one. In this case, at step A13, the timer T1 is caused to start its operation to count time interval (time interval Z1 in FIG. 7) between sphygmus and a flag "1" is set to the register L to indicate that the first sphygmus has been detected. Then operation goes back to step A2.

In this fashion, it is judged at step A8 that a flag "1" has been set to the register L and a judgment of time interval between ECG pulses is performed.

When the process goes from step A2 to A11 and sphygmus has been detected again, the operation goes to step A16, because a flag "1" has been set to the register L at step A12. At step A16, time data (time data Z1 in FIG. 7) counted by the timer T1 at A13 is transferred to the register C1. Then, the operation goes to step A17, where it is judged if a flag "1" has been set to the register N. When the flag "1" has not been set to the flag N or a flag "0" has been set to the register N, this is the case that no ECG pulse has been detected during time interval between adjacent two sphygmus. In this case, the operation goes to step A20 and gain data of the the register G0 is increased by a predetermined degree. Then, the operation goes to step A20, where gain data of the register G0 is increased by a predetermined degree, 1 and the operation goes back to step A1.

As described above, the gain of the variable-gain amplifier 42 is increased on the basis of gain data of the register G0. As a result, ECG wave shall easily be detected.

When it is judged at step A17 that the register has been set to a flag "1", this is the case that ECG pulse has been detected during time interval between two adjacent sphygmus. Then, the operation goes to step A18, where it is judged if "i≦C1≦j" is true. That is, it is judged if time data (time interval Z1 between pulses shown in FIG. 7) transferred to the register C1 shall fall in a range defined by constants i and j.

A judgment at steps A18 and process at steps A19 and A21 are similar to that at steps A10 and those at A11 and A15, respectively, except that the content of the register C1 is replaced by that of the register C0 and the process to the register G1 is performed in a similar manner to the register G0. In consequence, the variable-gain amplifier 52 in the sphygmus detecting section 15b is controlled in a similar manner to that 42 in the ECG wave detecting section 15a.

When it is judged at step A18 that i<C1<j, this is the case that a time interval (a content of the register C1 or transferred Z1) between normal sphygmus pulse waves has been detected. Then the operation goes to step A5, where it is judged that time data X1 has been transferred to the register C0 and further it is judged if a value of the register C1 is substantially equivalent to that of the register C0. When substantially equivalent, the operation goes to step A6, where sphygmus data (a number of sphygmus per minute) is calculated a time interval between the sphygmus pulse waves. The sphygmus data is transferred and stored in the sphygmus register 24, and is displayed on the display section 21.

When it is judged at steps A2 and A11 that neither ECG wave nor sphygmus wave has been detected, the operation goes to step A11, where, after it is judged that the timers T0, T1 are caused to start their operations respectively, a time measurement process is performed to increment a timer time.

Second Embodiment

Figure 8:
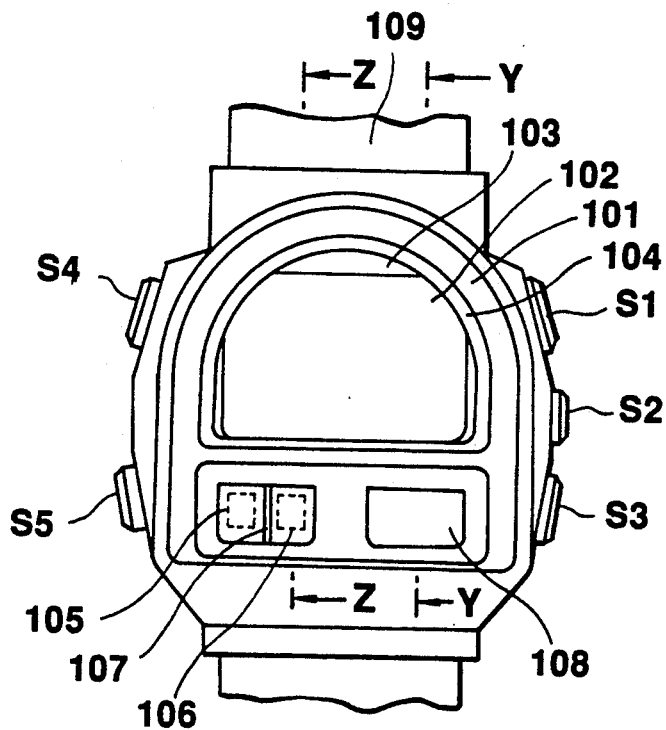
FIG. 8 is a view showing an external view of an electronic wrist watch employing the second embodiment of the present invention.

FIG. 8 is a view showing an external front view of an electronic wrist watch employing a second embodiment of the invention.

In FIG. 8, a wrist watch casing 101 is made of non-conductive synthesis resin. On the front surface of the electronic wrist watch is mounted a liquid crystal display device (hereafter, referred to as LCD) 102 covered with a watch glass 103. The watch glass 103 is fixed to the watch casing 101 with aid of packing member 104. The wrist watch casing 101 is provided in its left lower portion with a light emission diode (hereafter, referred to as LED) 105, a photo transistor 106 and a partition 107 which prevents the light emitted by LED 105 from being directly received by the photo transistor 106. In the right portion to these elements is embedded ECG wave (an electrocardiographic R wave) detecting electrode 108. Push button switches S1, S2, S3, S4 and S5 for switching display modes and entering basic data are mounted in the side wall of the wrist watch casing 101. At the upper and lower sides as viewed in FIG. 8 is fixed a watch strip 109.

Figure 9:
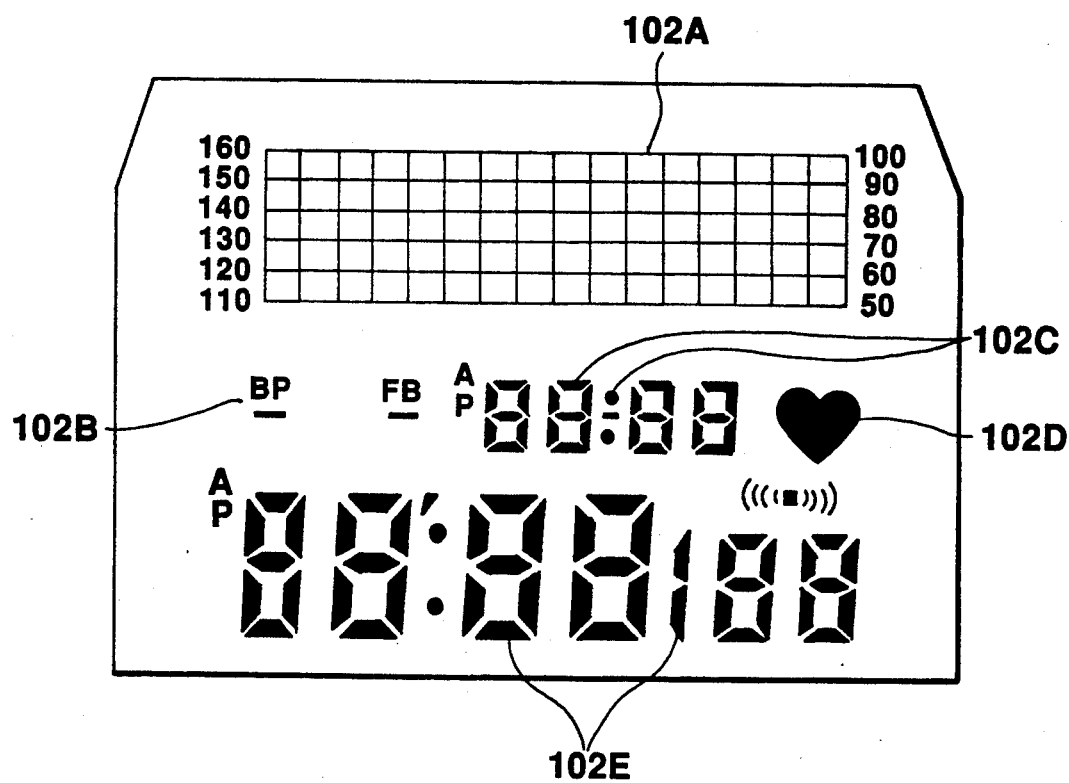
FIG. 9 is a view showing a liquid crystal display section of the wrist watch of FIG. 8 in detail.

A detailed construction of display electrodes of LCD 102 is shown in FIG. 9. LCD 102 is divided into three portions: upper portion, medium portion and lower portion. A dot-matrix display section 102A of 5 by 16 dots is mounted on the upper portion. Six numerals 160, 150, ... , 110 indicating the highest blood pressure are printed on the portion left to the dot-matrix display section 102A and six numerals 100, 90, ... , 50 for indicating the lowest blood pressure are printed on the portion right to the dot-matrix display section 102A. On the medium portion of LCD 102 are provided a mode display section 102B for indicating a current display mode, a small segment display member 102C for indicating sphygmus and a heart shaped display member 102D for indicating "under measurement" in a blinking manner. On the lower portion of LCD 102 are provided a large segment display member 102E for indicating a present time in a watch mode and indicating the highest blood pressure (or the lowest blood pressure) in a haemadynamometer mode. The large segment display member 102E comprises six digit segment display elements, a display element "1" disposed between the fourth and fifth digit segment display elements from the most significant digit, a display element ":" disposed between the second and third digit segment display elements and a display element for indicating "A and P".

Figure 10:
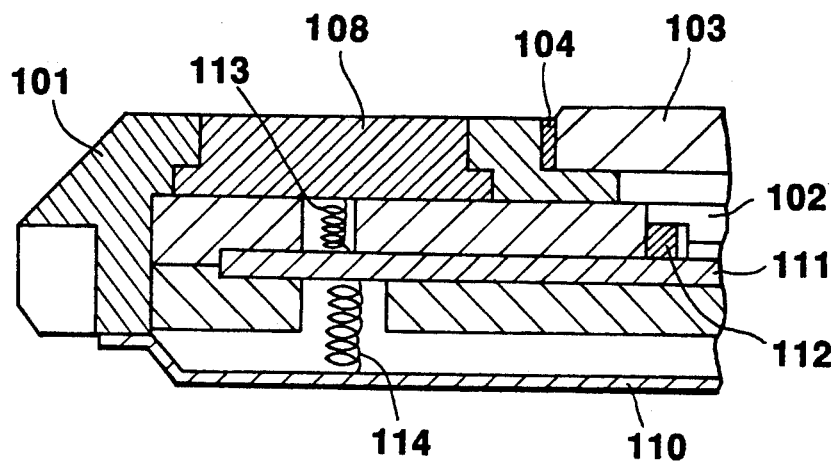
FIGS. 10 and 11 are views showing an internal construction of the electronic wrist watch of FIG. 8, respectively.
Figure 11:
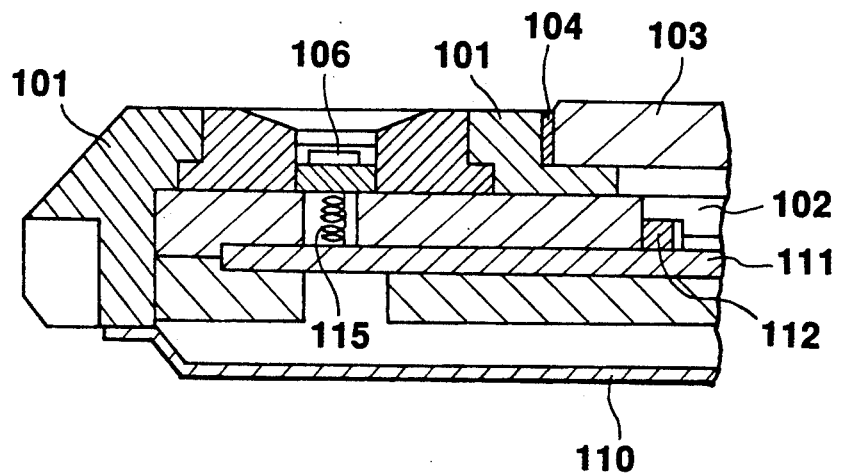

FIG. 10 is a partial cross-sectional view of an internal construction of the watch casing 101 taken along the line Y—Y of FIG. 8. FIG. 11 is a partial cross-sectional view of an internal construction of the watch casing 101 taken along the line Z—Z of FIG. 8. In FIG. 10, on the bottom portion of the watch casing 101 is mounted a rear cover 110, which is made from conductive material and serves as the other ECG wave detecting electrode. Within the watch casing 101 there is provided a circuit board 111, to which LCD 102 is connected through an inter connector 112. The ECG wave electrode 108 and the rear cover 110 are electrically connected to the circuit board 111 through conductive members 113, 114, respectively. As shown in FIG. 11, the photo transistor 106 is electrically connected to the circuit board 111 through a conductive member 115. Similarly, LED 105 of FIG. 8 is electrically connected to the circuit board 111 through a conductive member.

Figure 12:
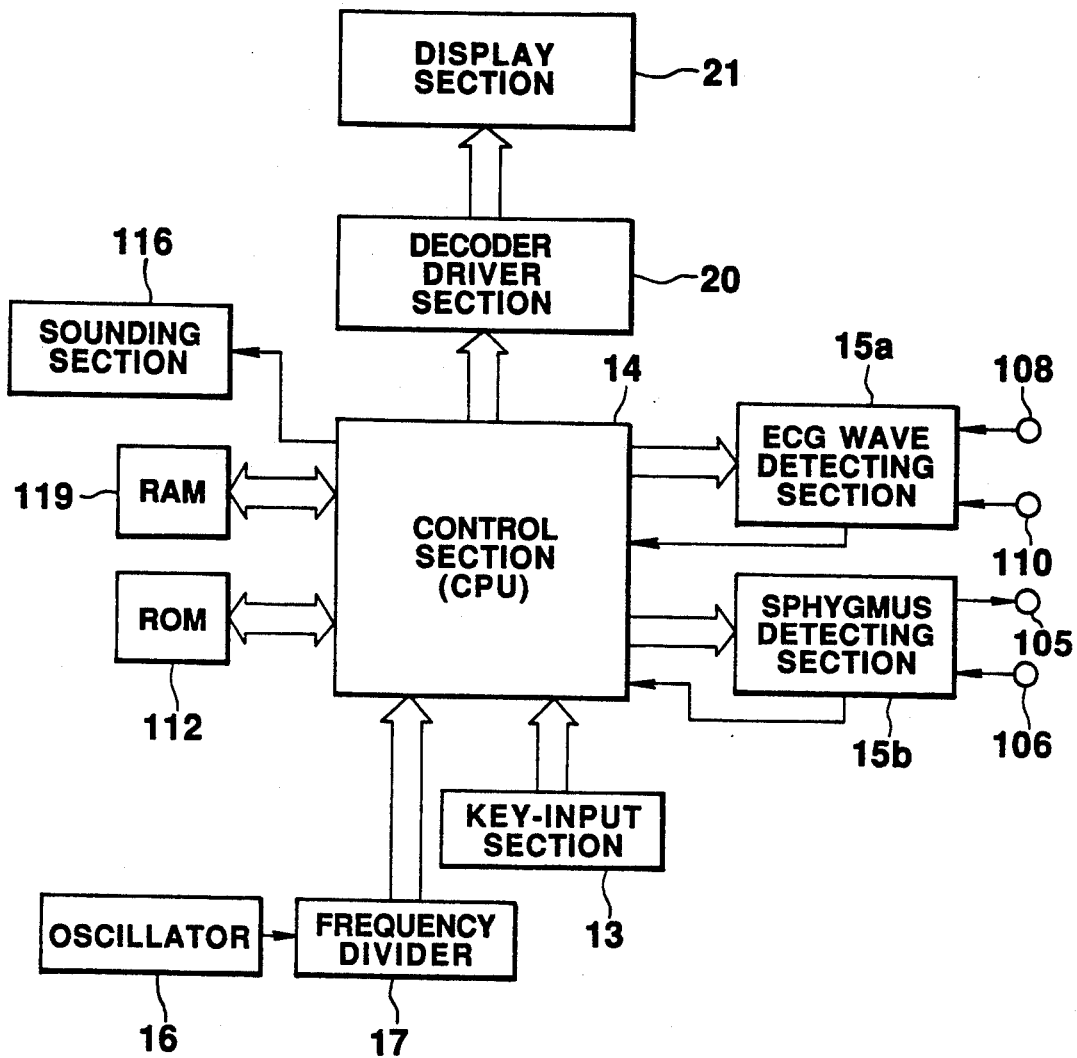
FIG. 12 is a circuit diagram of an internal circuit installed within the wrist watch of FIG. 8.

FIG. 12 is a block diagram of an internal circuit of the electronic wrist watch of FIG. 8. The internal circuit has a configuration substantially similar to the circuit of FIG. 3 except that a sounding section 116 is provided. Reference numerals of ECG wave electrodes (108, 110), LED (105) and the photo transistor (106) are different from those in FIG. 3. The internal construction of RAM 119 is different from that of RAM 19 shown in FIG. 3 and the process performed under control of a microprogram stored in ROM 112 is different from that of FIG. 3. Except the described above, like elements as those in FIG. 3 are designated by like reference numerals, and their description will be omitted.

Figure 13:
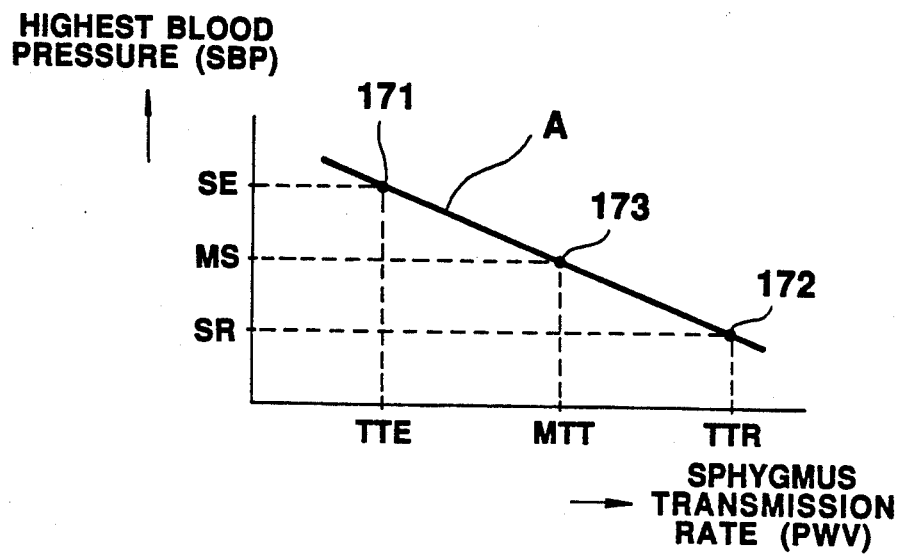
FIG. 13 is a view showing a relative relationship between the highest blood pressure and a sphygmus transmission rate.

The present embodiment is arranged to indicate the highest and lowest blood pressure. These blood pressures are not obtained by actual measurement of pressure in blood vessel, but obtained by performing calculation following the algorithm described below. FIG. 13 is a graph showing relation of the highest blood pressure (the y-axis) to the sphygmus transmission rate (the x-axis). When we draw a line through dots 171, 172 plotted in the graph of FIG. 13, we obtain the line A. The dot 171 is given by a value (SE) of the highest blood pressure of a subject measured right after his exercise and a sphygmus transmission rate (TTE) obtained while measuring of blood pressure while the dot 172 is given by a value (SR) of the highest blood pressure of the subject at rest and the sphygmus transmission rate (TTR) obtained while measuring the highest blood pressure of the subject at rest. It is known that dots given by values of the highest blood pressure and the corresponding sphygmus transmission rates, which are obtained by measuring the same subject in a state other than exercising or resting, tend to converge on the line A. Therefore, if the value (SE) of the highest blood pressure and the sphygmus transmission rate (TTE) of a subject right after exercise and those, (SR) and (TTR), of the same subject at rest are measured and the line drawn through dots given by the measured values is memorized, a highest blood pressure would be calculated from a measured sphygmus transmission rate using the previously memorized line A. For instance, when a sphygmus transmission rate (MTT) is measured, a value of blood pressure (MS) corresponding to the value (MTT) will be obtained from a dot 173 on the line A. The value thus obtained will represent the highest blood pressure of the subject.

The above line A may be expressed by a linear expression: $y = ax + b$, where a and b are constants. The constants a, b are calculated by the control section 14 as described below. That is, values SE, SR of the highest blood pressure of a subject just after exercise and at rest are measured by another precise haemadynamometer, respectively and these measured values are entered to CPU 14, and sphygmus transmission rates TTE, TTR are measured from sphygmus and ECG waves obtained at the measurements of respective values of the highest blood pressure. Then, the control section 14 calculates these constants, a and b, by operation of the switch S5 and stores them in the registers of RAM 112. After input of the values of the highest blood pressure and the measurement of sphygmus transmission rates, the control section 14 calculates a value y or the value MS of the highest blood pressure by substituting a value MTT for x of the linear expression $y = ax + b$. Therefore, only measurement of the sphygmus transmission rate MTT is required to calculate the value MS of the highest blood pressure.

Figure 14:
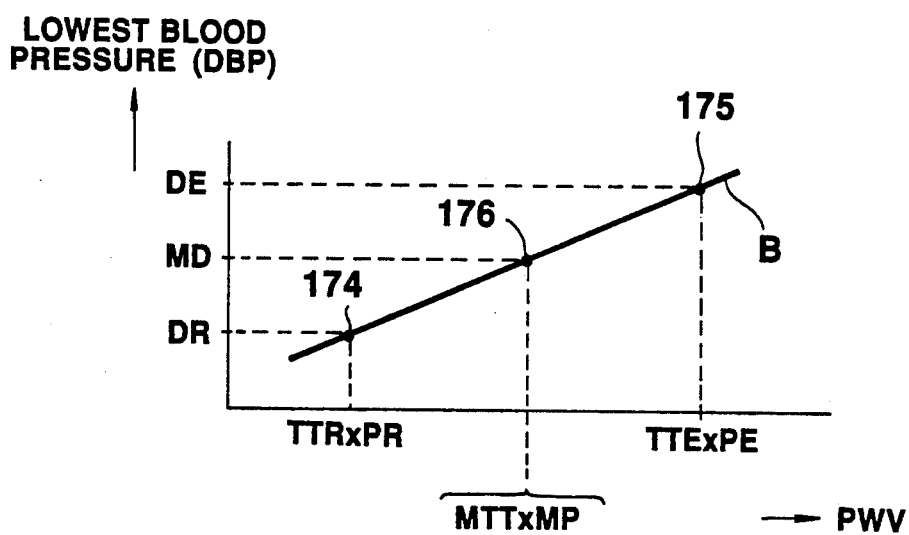
FIG. 14 is a view showing a relative relationship between the lowest blood pressure and the sphygmus transmission rate.

FIG. 14 is a graph showing relation of the lowest blood pressure (the y-axis) to a product (the x-axis, a number of sphygmus per minute) of the sphygmus transmission rate and the sphygmus data. When we draw a line through dots 174, 175 plotted in the graph of FIG. 14, we obtain the line B. The dot 174 is given by a value (DR) of the lowest blood pressure of a subject measured while he is at rest and a product of a sphygmus transmission rate (TTR) and sphygmus data (PR) both obtained while measuring of the lowest blood pressure. Meanwhile, the dot 175 is given by a value (DE) of the lowest blood pressure of the subject measured right after his exercise and a product of a sphygmus transmission rate (TTE) and sphygmus rate (PE) both obtained while measuring the lowest blood pressure of the subject. It is known that dots given by values of the lowest blood pressure and a product of the corresponding sphygmus transmission rates and sphygmus data, which are obtained by measuring the same subject in a state other than exercising or resting, have a tendency to converge on the line B. Therefore, if the value (DR) of the lowest blood pressure, and the sphygmus transmission rate (TTR) and sphygmus data of a subject at rest and those (DE), (TTE) and (PE) of the same subject right after his exercise are previously measured using a precise haemadynamometer and a linear expression of the line B drawn through dots given by these obtained values is memorized, a lowest blood pressure (MD) would be calculated from a measured sphygmus transmission rate (MTT) and sphygmus data (MT) using the previously memorized linear expression. That is, the lowest blood pressure (MD) expressed by a dot 176 on the line B may be calculated from a product of the sphygmus transmission rate (MTT) and sphygmus data (MT) obtained by measuring sphygmus and ECG wave.

The line B may be expressed by a linear expression $y = mx + n$, where m, n are constants, which are stored in the registers of RAM 112 respectively. A value y, i.e., a value (MD) of the lowest blood pressure may be calculated by substituting the product, MTT x MP, of the sphygmus transmission rate MTT and the sphygmus MP for x of the linear expression $y = mx + n$.

Figure 15:
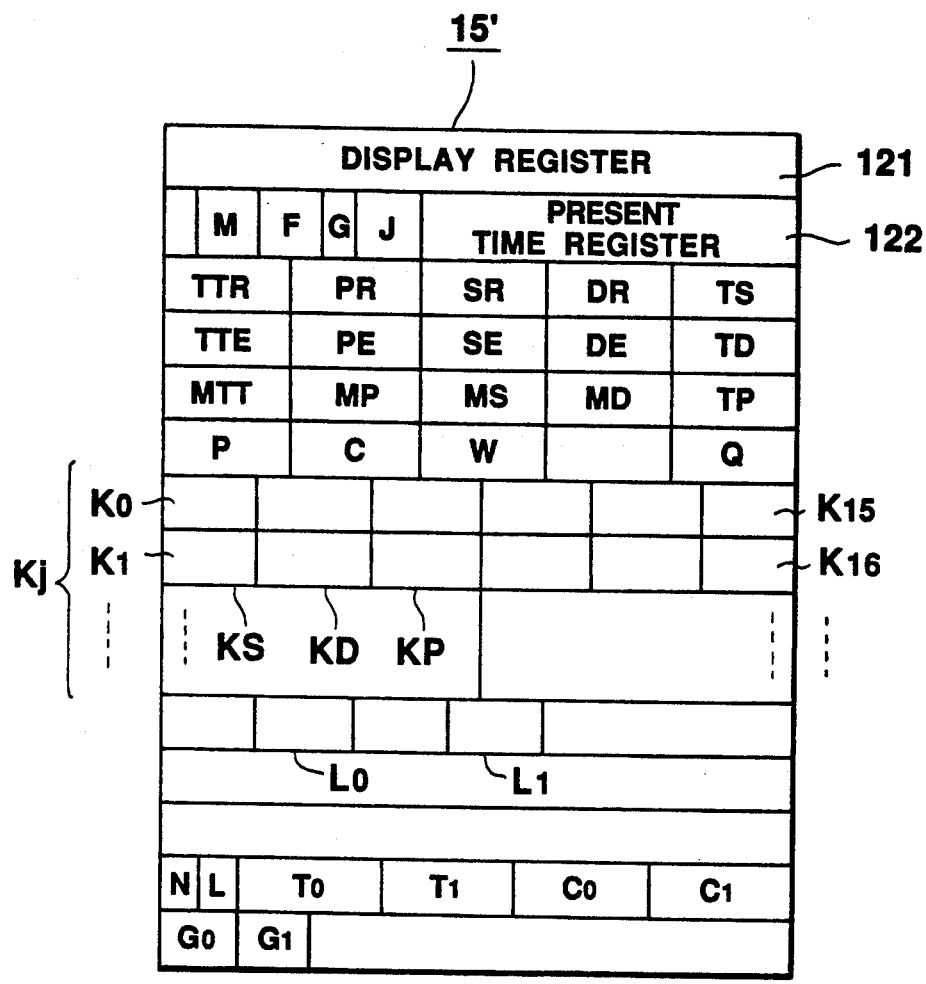
FIG. 15 is a view showing an internal construction of RAM of FIG. 12.

FIG. 15 is a view showing an internal construction of RAM 119. A display register 121 serves to store display data to be displayed on LCD 102 of the display section 20. A present time register 122 serves to store present time counted on the basis of a time counting signal supplied from the frequency divider circuit 17. A register M serves to store a value "0", "1" or "2", each corresponding to one of the fundamental display modes (a watch mode, a haemadynamometer mode and a bio feed-back mode). A register F is a register, which, in a haemadynamometer mode of M="1", stores a value "0" in a normal measurement mode, a value "1" in measurement mode of a subject at rest and a value "2" in a measurement mode of a subject right after his exercise and which, in a bio recall mode of M="2", stores a value "0" in a bio selecting mode shown in FIG. 15, a value "1" in bio setting mode and a value "2" in a bio measurement/display mode. A register G serves to store a value "1" during bio measurement. A register J serves to store a value for selecting a figure to be set. A register TTR serves to store a time-interval data of a subject at rest. A register PR serves to store sphygmus data of the subject at rest. A register SR serves to store highest blood pressure data of the subject at rest. A register DR serves to store lowest blood pressure data of the subject at rest. A register TTE serves to store time interval data of the subject right after his exercise. A register PE serves to store sphygmus data of the subject right after his exercise. A register SE serves to store highest blood pressure data of the subject right after his exercise. A register DE serves to store lowest blood pressure data of the subject right after his exercise. A register MTT serves to store time interval data during measurement. A register MP serves to store sphygmus data during measurement. A register MS serves to store highest blood pressure data during measurement. A register MD serves to store lowest blood pressure data during measurement. A register TS serves to store the highest blood pressure data which have been set. A register TD serves to store the lowest blood pressure data which have been set. A register TP serves to store the sphygmus data which have been set. A register P is for designating a register Kj as will be described later. A register W is a register for a timer. A register C is a 10-sec timer. A register Q is to store a value for designating data (one of highest blood pressure, lowest blood pressure and sphygmus) to be measured. Registers Kj (j=0, 1, 2, ... n) include a number of registers K0, K1, K2, ... Kn, each provided with register sections KS, KD and KP. The register section KS stores measured highest blood pressure data, the register section KD stores measured lowest blood pressure data and the register KP stores measured sphygmus data. A register L0 is a register which stores two constants defining a relation between the highest blood pressure and the sphygmus transmission rate. A register L1 is a register which stores two constants defining a relation between the lowest blood pressure, the sphygmus transmission rate and the sphygmus. The registers N, L, T0, T1, C0, C1, G0 and G1 are similar registers shown in FIG. 4, respectively.

Now, operation of the switches S1 to S4 for switching the display mode will be described.

A value of the register M is changed by operation of the switch S1 from "0" to "1", from "1" to "2" and from "2" to "0". Responding to a change of the value of the register M, the display mode is changed from "a watch mode" of M10 to "a haemadynamometer mode" of M20, from "a haemadynamometer mode" of M20 to "a bio feed back mode" of M30 and from "a bio feed back mode" of M30 to "a watch mode" of M10, as shown in FIG. 16.

In the watch mode of M10, a present time data, "SUN '91, 1 (Jan.) 6th, 10:57 23", are displayed on LCD 102.

When a value "1" has been set to the register M, i.e., the haemadynamometer mode" of M20 has been set, by operation of the switch S1, a value of the register F is changed by operation of the switches S2 to S4 and the display mode is further changed. When "the haemadynamometer mode" of M=1 has been set and the register F has been set t a value "0", the normal measurement mode is set. In the normal measurement mode, a notice "OK !" is displayed on the dot-matrix display section 102A of LCD 102 and a notice "BP" with under bar is displayed on a mode display section 102B for indicating that the normal measurement mode has been set, a character "P" is displayed for indicating sphygmus, and further "—" display member 102C and a heart shaped display member 102D are turned on in a blinking manner. In this normal measurement mode, when the right middle finger of a subject is put on the ECG wave detecting electrode 108 and the right index finger of the subject is put on the sphygmus detecting section comprising the photo transistor 106 and LED 105, a blood pressure is calculated by performing an operation on the detected ECG wave and sphygmus, as will be described in detail. As a result, for example, as shown at MD22 of FIG. 16, a notice of "sphygmus (a number of sphygmus per minute) 63, highest blood pressure 122, lowest blood pressure 70" is displayed and after a certain period of time, the display returns to that of MD21.

Figure 16:
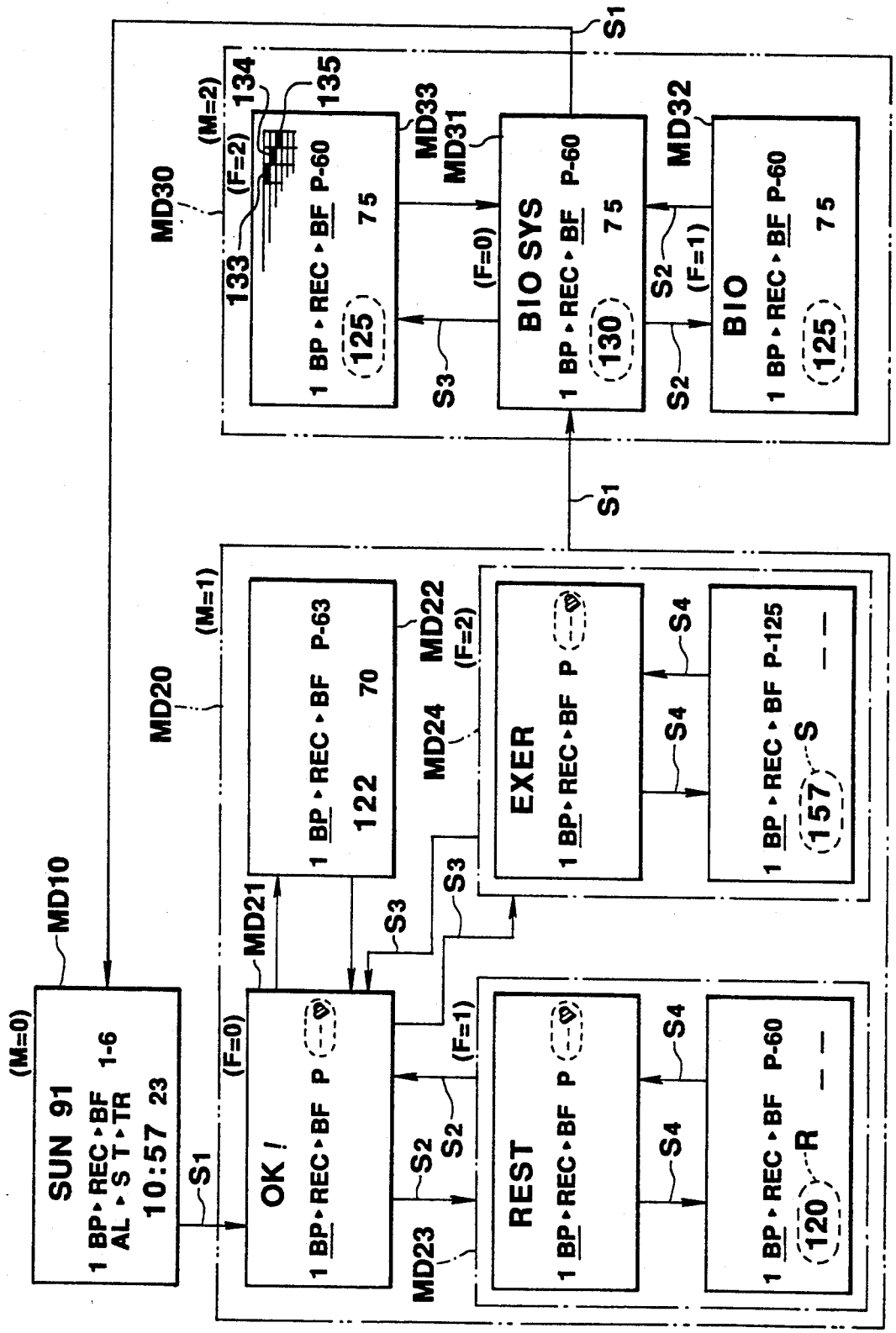
FIG. 16 is a view for describing a display mode, and showing displays switched by a switching operation

When the display mode of M=1 and F=0 shown at MD21 of FIG. 16 has been set, and the pertinent indication is displayed, operation of the switch S2 switches a value of the register F to "2" and the display is switched to the display in the measurement at-rest mode as shown at MD23 of FIG. 16. In the measurement at-rest mode, the indication "OK !" of MD21 is switched to a indication "REST". In the measurement at-rest mode, the highest and lowest blood pressure of the subject at rest, and so on are measured and input to the control section 14, which will be described later in detail.

When the display of MD21 of FIG. 16 is on, operation of the switch S3 switches a value of the register F to "3" and the display mode is switched to the measurement right-after-exercise mode shown at MD 24. In the measurement right-after-exercise mode, the notice "OK !" in the bio measurement mode of MD 21 is switched to a notice of "EXER" (an abridgment of "exercise") indicating that the subject is right after his exercise. In the measurement right-after-exercise mode, the highest and lowest blood pressure of the subject right after exercise, and so on are measured and input to the control section 14, which will be described later in detail.

When the display of M=2 in the bio feed back mode of MD30 of FIG. 16 is on, every operation of the switch S2 changes a value of the register F from "0" to "1" or from "1" to "0". When the register F has a value "1", the display in the bio setting mode shown at MD32 of FIG. 16 is on. When the switch S3 is operated, the value of the register F is switched from "0" to "2" and from "2" to "0". When F="2", the display in the bio display mode is on, as shown at MD33 of FIG. 16.

Referring to the flowcharts shown in FIGS. 17 to 19, various processes performed in the above described display modes under control of the control section 14 will be described in detail.

Figure 17:
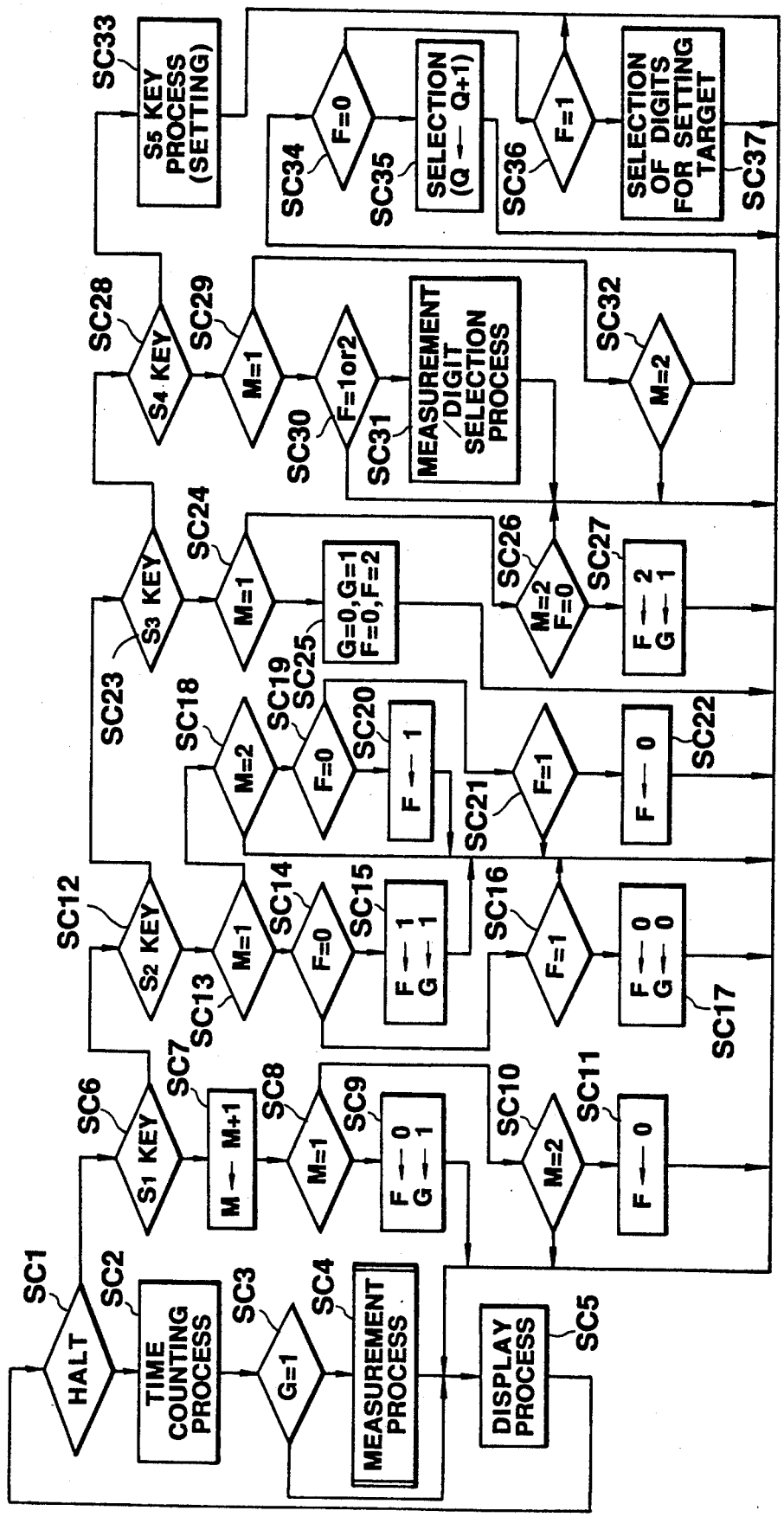
FIG. 17 is a main flowchart showing a whole program flow.

FIG. 17 is a flowchart showing a whole program flow.

Time Counting and Measuring Process

Processes will be described, that are performed every time time-counting signals are received from the frequency divider circuit 17.

When an input signal is entered from the key input section 12 in a HALT state at step SC1 of FIG. 17, the operation goes to step SC6 while, when a time counting signal is entered from frequency divider circuit 17 in the HALT state at step SC1, the operation goes to step SC2, where a time counting process is performed and the result of the time counting process, i.e., present time data, is stored in the present time register 122 of RAM 119. At step SC3, it is judged if the register G has been set to a value "1", i.e., if G=1 is true. When G=1 is true, it is judged that measurement of blood pressure and sphygmus is going on and the operation goes to step SC5, where display processes are performed in accordance with values of the registers M, F shown in FIG. 16. Then, the operation returns to step SC1.

When it is judged at step SC3 that G=1 is not true, the operation goes directly to step SC5, where the display process is performed.

During the above process, when the time-counting timing is reached, the time counting process is performed and the counted present-time data is stored in the present time resister 122 of RAM 112. When G=1 is true, measurement of blood pressure is performed, as will be described in detail while G=1 is not true, i.e., G=0 is true, no measurement process is performed.

Display-Mode Switching Process

Now, switching processes for switching the display mode by operation of the switches S1 to S4 will be described. That is, changing processes for changing the values of the registers F, M will be described.

When a key input signal is entered from the key input section 12 in HALT state at step SC1, the operation goes to step SC6, where it is judged if the switch S1 has been operated, i.e., if the key input signal has been supplied from the switch S1. When the switch S1 has been operated, the control section 14 performs the operation at step SC7, where the display mode is switched cyclically from the watch mode through the haemadynamometer mode and the bio feed-back mode, and again to the watch mode. That is, the operation of the control section 14 goes to step SC8, where a value "1" is added to a value of the register M to change the display mode to the following mode. Then, the operation goes to step SC8, where it is judged if the value of the register M is "1", i.e., if M=1 is true. When M=1 is true, the display mode changes the display from the watch mode to the haemadynamometer mode. In this case, the operation goes to step SC9, where a value "0" is set to the register F, setting the normal measurement mode of MD21 of FIG. 16, and further a value "1" is set to the register G, for measuring blood pressure. Then, the operation goes to step SC5.

During the above process, the watch mode is changed to the haemadynamometer mode and values "1" and "0" are set to the registers M and F, respectively. Then, the display of the normal measurement mode is on as shown at MD21 of FIG. 16. Further, as a value "1" is set to the register G, the measurement process is performed at step SC4, as will be described later.

When it is judged at step SC8 that M=1 is not true, the operation goes to step SC10, where it is judged if M=2 is true. When M=2 is true, the haemadynamometer mode is changed to the bio feed-back mode. Then, the operation goes to step SC11, where a value "0" is set to the register F and the bio selection mode of MD31 is selected from among the bio feed back mode of MD30 shown in FIG. 16. The operation goes to the display process at step SC5.

As described above, the haemadynamometer mode is changed to the bio feed back mode and values "2" and "0" are set to the registers M and F, respectively. Then, the bio selection mode is displayed as shown at MD31 of FIG. 16.

When it is judged at step SC10 that M=2 is not true, i.e., M=0 is true, the bio feed back mode is changed to the watch mode. The operation goes to the display mode at step SC5.

During the process described above, the bio feed back mode is changed to the watch mode and a value "0" is set to the register M. Then, the watch mode of MD10 of FIG. 16 is displayed.

When, at step SC6, it is judged that the switch S1 has not been operated, i.e., that no key input signal is supplied from the switch S1, the operation goes to step SC12, where it is judged if the switch S2 has been operated, i.e., if a key input signal has been supplied from the switch S2. When it is judged that a key input signal has been supplied from the switch S2, the operation goes to step SC13, where it is judged if a value "1" has been set to the register M, i.e., if M=1 is true. When M=1 is true, the operation goes to step SC14, where it is judged if F=0 is true. When F=0, the normal measurement mode of MD21 has been selected from among the haemadynamometer mode. Then, the operation goes to step SC15, where a value "1" is set to the register F and the normal measurement mode is switched to the measurement at-rest mode, and further a value "1" is set to the register G for measuring blood pressure. Thereafter, the operation goes to the display process at step SC5.

When it is judged at step SC14 that F=0 is not true, the operation goes to step SC16, where it is judged if F=1 is true. When F=1, the measurement at rest mode of MD 23 of FIG. 16 has been set in accordance with M=1 and F=1. The control section 14 judges that a key input signal of the switch S2 is an instruction for changing the measurement at-rest mode to the normal measurement mode, and goes to the operation at step SC16. The control section 14 sets a value "0" to the register F, switching to the normal measurement mode and further sets a value "0" to the register G, existing from the measurement mode. Now, the control section goes to the display mode at step SC5. Judging at step SC16 that F=1 is not true, the control section 14 judges that the key input signal of the switch S2 is ineffective, and goes to step SC5.

As described above, when the switch S2 is operated in the blood pressure measurement mode, the normal measurement mode of MD21 and the measurement at-rest mode are alternatively selected. As G=1 is true in the measurement at-rest mode, the measurement process of blood pressure is performed at step SC4, as will be described later. When neither the normal mode nor the measurement at-rest mode has been set in the haemadynamometer mode, the key input signal of the switch S2 is ignored.

When it is judged at step SC13 that M=1 is true, the operation goes to step SC18, where it is judged if the key input signal of the switch S2 has been entered at M=2. When it is judged that the key input signal of the switch S2 has been entered at M=2, the operation goes to step SC19, where it is judged if F=0 is true. When F=0 is true, the bio selection mode of MD31 has been selected from among the bio feed-back mode, and it is judged that the bio selection mode is to be changed to the bio setting mode of MD32. Then, the operation goes to step SC20, where a value "1" is set to the register F, setting the bio setting mode, and further goes to the display process at step SC5.

When it is judged at step SC19 that F=0 is not true, the operation goes to step SC21, where it is judged if F=1 is true. When F=1 is true, the bio setting mode of MD32 has been set in accordance with M=2 and F=1 and it is judged that the bio setting mode is to be changed to the bio selection mode. Then, the operation goes to step SC22, where a value "0" is set to the register F, switching the bio setting mode to the bio selection mode, and the process goes to the display process at step SC5. When it is judged at step SC21 that F=1 is not true, the key input signal of the switch S2 is ignored and the operation goes directly to step SC5.

As described above, when the key input signal of the switch S2 is entered in the bio feed-back mode, the bio selection mode of MD31 and the bio setting mode of MD32 are alternatively selected. When neither the bio selection mode nor the bio setting mode has been set, the key input signal of the switch S2 is ignored.

When it is judged at step SC18 that M=2 is not true, then the operation goes directly to step SC5.

As described above, when neither the haemadynamometer mode nor the bio feed-back mode has been set, the key input signal of the switch S2 is ignored.

When it is judged at step SC12 that no key input signal of the switch S2 is entered, the operation goes to step SC23, where it is judged if a key input signal of the switch S3 is entered. When it is judged that the key input signal of the switch S3 is entered, the operation goes to step SC24, where it is judged if the key input signal of the switch S3 has been entered in the display mode of M=1. When M=1 is true, the haemadynamometer mode has been set and it is judged that the key input signal of the switch S3 has instructed to alternatively select the normal measurement mode and the measurement right-after-exercise mode, and then the operation goes to step SC25. When it is judged at step SC25 that F=0 is true, a value "2" is set to the register F, changing the normal measurement mode to the measurement right-after-exercise mode, and a value "1" is set to the register G. When F=2, a value "0" is set to the register F, changing the measurement right-after-exercise mode to the normal measurement mode, and a value "0" is set to the register G.

As described above, when the key input signal of the switch S3 is entered in the haemadynamometer mode, the normal measurement mode of MD21 and the measurement right-after-exercise mode are alternatively switched. A value "1" is set to the register G in the measurement right-after-exercise mode, the operation goes to step SC4 to perform the measurement of blood pressure.

When it is judged at step SC24 that M=1 is not true, the operation goes to step SC26, where it is judged if a key input signal of the switch S3 has been entered in the display mode of M=1 and F=0. When it is judged that the key input signal of the switch S3 has been entered in the display mode of M=1 and F=0, the bio selection mode of MD31 has been selected from among the bio feed-back mode and therefore it is judged that the key input signal of the switch instructs to switch the display mode from the bio selection mode to the bio measurement display mode. The operation goes to step SC27, where a value "2" is set to the register F, setting the bio measurement display mode, and a value "1" is set to the register G for measuring bio of blood pressure data, and then the operation goes to step SC5. When it is judged at step SC26 that M=2 and F=0 are not true, the key input signal of the switch S3 is ignored and the operation instantly goes back to step SC5.

As described above, when the key input signal of the switch S3 is entered in the bio feed-back mode, the bio selection mode of MD31 and the bio measurement display mode of MD33 are alternatively switched. The key input signal of the switch S3 entered not in the bio measurement display mode is ignored. Similarly, the key input signal of the switch S3 entered neither in the blood pressure measurement mode nor in the bio feed back mode is also ignored.

Now, entry of blood pressure data will be described in detail, which are measured with a precise haemadynamometer.

Referring to the flowchart of FIG. 17, when operation of the switch S4 is detected at step SC28, the operation goes to step SC29. When it is judged at step SC29 that $M=1$ is true, the operation goes to step SC30, where it is judged if $F=1$ or $F=2$ is true. When it is judged that $F=1$ or $F=2$ is true, it is judged that a key input signal of the switch S4 is entered in the measurement at-rest mode or the measurement right-after-exercise mode of the haemadynamometer mode of MD20 and that selection of digits is instructed for entering and setting data of a subject measured while he is at rest or right after exercise. Then, the operation goes to step SC31, where a digit selection process is performed for measuring and entering data, and goes back to the display process of SC5.

As described above, the digit selection is allowed to be performed in the measurement at-rest mode or in the measurement right-after-exercise mode of FIG. 16 for entering data including blood pressure data, which are measured by the key input signal of the switch S4. The digit selection process (not shown) is successively performed on the basis of a value of the register J. The register J is added with a value "1" every operation of the switch S4. $J=0$ indicates that measurement of ECG waves and sphygmus is going on while the highest blood pressure of a subject at rest or right after exercise is being measured. When the switch S4 is operated at $J=0$, a value "0" is set to the register G and a flag is set to indicate completion of the above measurement. Further, a value "1" is added to the register J, selecting digits for entering and setting data. In the digit selection process, since $J=1$ at first, the digits are selected for the highest blood pressure and the digits selected for the highest blood pressure are displayed in a blinking manner as shown at R and S ("120" and "157") in FIG. 16. The following operation of the switch S4 adds "1" to the register J, setting $J="2"$. The digit selecting process is prepared for entering and setting the lowest blood pressure data. The further operation of the switch S4 sets $J=3$ and the digit selection process is designated for entering and setting sphygmus data. Further another operation of the switch S4 completes entry of measured blood pressure data. Data are set to the selected digits in the setting process in response to operation of the switch S5.

When it is judged at step SC30 that $F=1$ or $F=2$ is not true, the operation goes to step SC5. More particularly, when neither the measurement at-rest mode nor the measurement right-after-exercise mode has been set in the haemadynamometer mode, the key input signal of the switch S4 is ignored.

Now, a target selecting and setting process will be described for performing bio measurement.

When it is judged at step SC29 that $M=1$ is not true, the operation goes to step SC32, where it is judged if the key input signal of the switch S4 has been entered in the bio recall mode of $M=2$. When the result of the judgement is YES, the operation goes to step SC34, where it is judged if the key input signal of the switch S4 has been entered at $F=0$. When YES, it is judged that the key input signal of the switch S4 has been entered in the bio selection mode of MD31 among the bio recall mode of MD30 of FIG. 16, and that the digit selection process is designated with respect to bio data to be measured for performing a bio measurement display. Then, the operation goes to step SC35, where a value "1" is added to the register Q, selecting digits for bio data to be measured, and goes back to the display process at step SC5.

As described above, the key input signal of the switch S4 entered in the bio selection mode of FIG. 16 allows digits to be selected for bio data to be measured. The digit selection process is successively performed on the basis of the value of the register Q. Every key input signal of the switch S4 adds a value "1" to the register Q. More particularly, digits (130) for the highest blood pressure are selected at $Q=1$ and digits for the highest blood pressure are displayed in a blinking manner, as shown at MD31 in FIG. 16. Another key input signal of the switch S4 adds a value "1" to the register Q, setting $Q=2$ and digits are selected for the lowest blood pressure. Yet another key input signal of the switch S4 further adds a value "1" to the register Q, setting $Q=3$ and digits are designated for sphygmus data. After the mode is changed by operation of the switch S2, the target data are set to the selected digits by operation of the Switch S4.

When it is judged at step SC34 that $F=0$ is true, the operation goes to step SC36, where it is judged if $F=1$ is true. When YES, the operation goes to step SC37, where the target data are allowed to be set to the digits selected at step SC35, as the bio setting mode of MD32 has been set. By operation of the switch S5, the target data are set to work areas (not shown) of RAM 119 or to particular registers of the register Kj of RAM 119, for example, to register sections corresponding to the selected digits among the register sections KS, KD, KP of the register KO.

As described above, the key input signal of the switch S4 entered in the bio setting mode allows a target value of bio data to be set.

When it is judged at step SC36 that $F=1$ is not true, the operation goes to step SC5.

In this case, when neither the bio selection mode of MD31 nor the bio setting mode of MD32 has been set in the bio feed back mode of FIG. 16, then the key input signal of the switch S4 is ignored.

When the key input signal of the switch S4 is not entered at step SC28, it is judged that a key input signal of the switch S5 has been entered, and the operation goes to step SC33 to perform a pertinent process. For example, in the bio setting mode of $M=2$ and $F=1$ a target value is set to the selected digits. In this setting process, data allowed to be set at step SC37 is set to the digits selected at step SC36. At completion of the process, data measured, selected and entered at step SC31 are stored in the registers SR, DR and PR or in the registers SE, DE and PE of RAM 119 by operation of the switch S5. Further, constants calculated as described above are stored in the registers L0, L1.

As described above, when the measurement at-rest mode or the measurement right-after-exercise mode in the haemadynamometer mode of FIG. 16 has been set and digits have been selected by the key input signal of the switch S4, data hare stored in the selected digits by the key input signal of the switch S5. When the bio setting mode of MD32 has been set and the target data are allowed to set to the selected digits by operation of the switch S4, data are set to the selected digits by operation of the switch S.

Measurement Process of Blood Pressure Data

When the register G has been set to a value "1" by operation of the switches S1 to S5, it is judged at step SC3 that G=1 is true and a measurement process of blood-pressure data is performed. While when it is judged that G=0, the display process is performed. In the measurement process of blood pressure data, ECG wave and sphygmus are measured to obtain the highest and lowest blood pressure data. That is, the measurement process of blood pressure data is performed at the time when the highest blood pressure and the lowest blood pressure data at rest and right after exercise are entered, the measurement process of blood pressure data is performed at the time when measurement is performed in the normal measurement mode of MD22 of FIG. 16 using the entered highest and lowest blood pressure data, or the measurement process is performed in the bio measurement display mode of MD33 of FIG. 16 similarly using the entered highest and lowest blood pressure data.

Now, the measurement process of blood pressure data at step SC4 will be described in detail, referring to the flowchart of FIG. 18.

Figure 18:
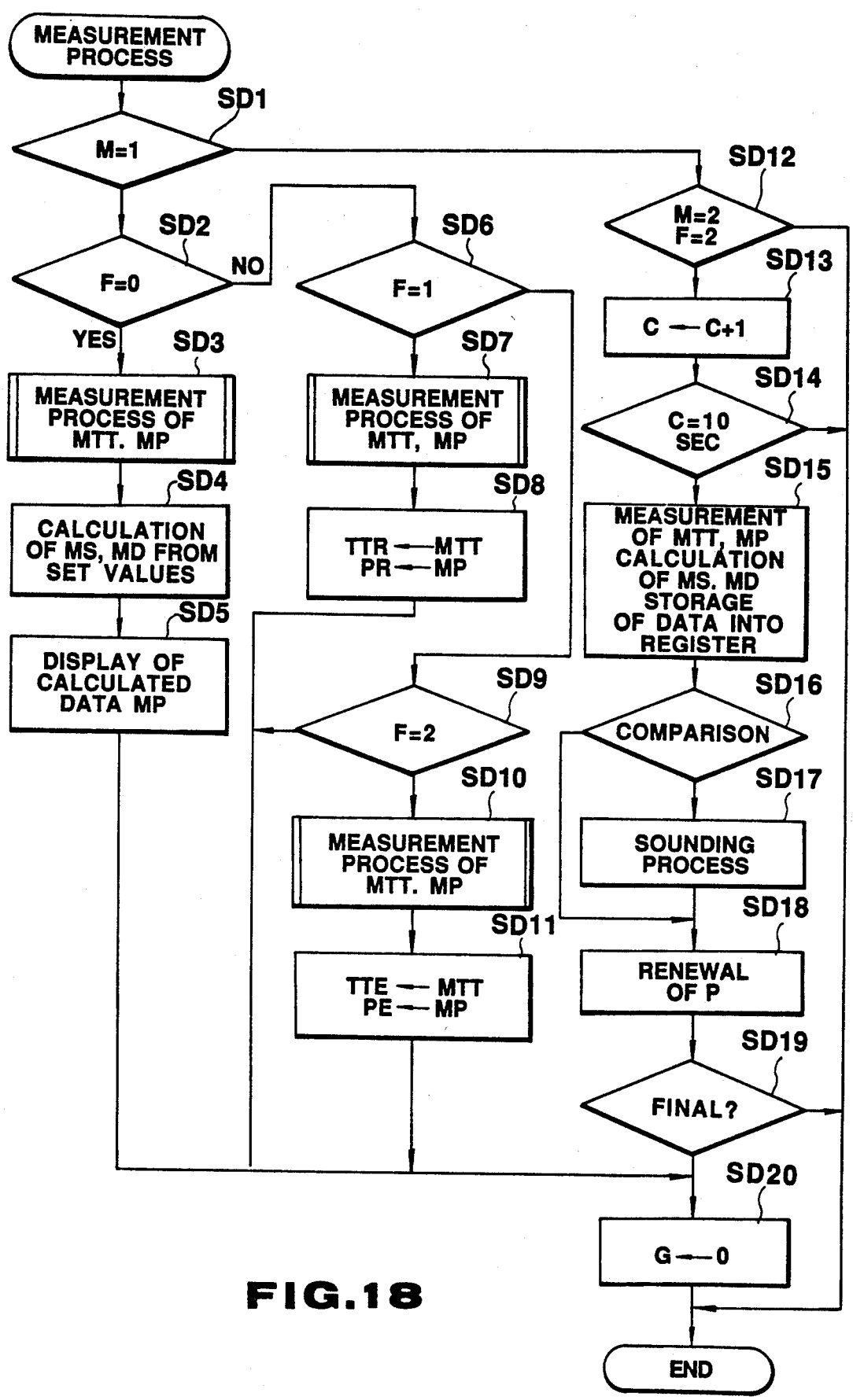
FIG. 18 is a flowchart showing a measurement process in the main flowchart of FIG. 17 in detail.

It is judged at step SD1 of FIG. 18 if M=1 is true. When M=1 is true, the operation goes to step SD2, where it is judged if F=2 is true. When F=2 is true, it is judged that the normal measurement mode of MD21 of FIG. 16 has been set in accordance with M=1 and F=1, and the operation goes to step SD3. At step SD3, a measurement process of MTT and MP (sphygmus transmission rate, sphygmus) is performed, as will be described in detail with reference to FIG. 19 and the operation goes to step SD4. At step SD4, the highest and lowest blood pressure data are calculated from values (the constants a, b and m, n of the linear expressions representative of the lines A and B of FIGS. 13, 14) stored in the registers L0, L1 of RAM 119 and the calculated data are stored in the registers MS, MD of RAM 119. Then, the operation goes to step SD5, where the calculated highest blood pressure data and lowest blood pressure data, and the measured sphygmus data are displayed, and further goes to step SD20. At step SD20, the register G is reset to a value "0", indicating the measurement process of blood pressure has been completed, and the operation returns to the main flow of FIG. 17.

As described above, the highest blood pressure and the lowest blood pressure are displayed in the mode of MD21 of FIG. 16.

When it is judged at step SD2 that F=0 is not true, the operation goes to step SD6, where it is judged if F=1 is true. When F=1 is true, it is judged that the measurement at-rest mode of the haemadynamometer mode has been set. At step SD7, a measurement process of MTT.MP is performed and the operation goes to step SD8, time interval data and sphygmus data measured and stores in the registers MTT, MP are stored in the registers TTR, PR of RAM 119, respectively, and the operation goes back to the main flow of FIG. 17 and the display process at step SC5 is performed.

As described above, when M=1 and F=1 are true, the measurement at rest mode of the haemadynamometer mode has been set. In the measurement at rest mode, ECG wave detecting section 15a and sphygmus detecting section 15b perform the measurement process of MTT and MP to detect time interval data representative of sphygmus transmission rate and sphygmus data, respectively. Data thus measured are stored in the registers TTR, PR of RAM 118, respectively.

When it is judged at step SC6 that F=1 is not true, the operation goes to step SC9, where it is judged if F=2 is true. When F=2 is true, it is judged that the measurement right-after-exercise mode of the haemadynamometer mode has been set. At step SD10, the measurement process of MTT, MP is performed and the operation goes to step SD11, time interval data and sphygmus data measured and stored in the registers MTT, MP are stored in the registers TTE, PE of RAM 119, respectively. Then, the operation goes back to the main flow of FIG. 17 and the display process at step SC5 is performed.

As described above, when it is judged that M=1 and F=2 are true, the measurement right-after-exercise mode of the haemadynamometer mode has been set. In the measurement at right-after-exercise mode, ECG wave detecting section 15a and sphygmus detecting section 15b detect time interval data representative of sphygmus transmission rate and sphygmus data. Data thus measured are stored in the registers TTE, PE of RAM 119, respectively.

Now, referring to the flowchart of FIG. 19 the measurement process of MTT, MP at steps SD3, SD7 and SD10 will be described in detail.

Figure 19:
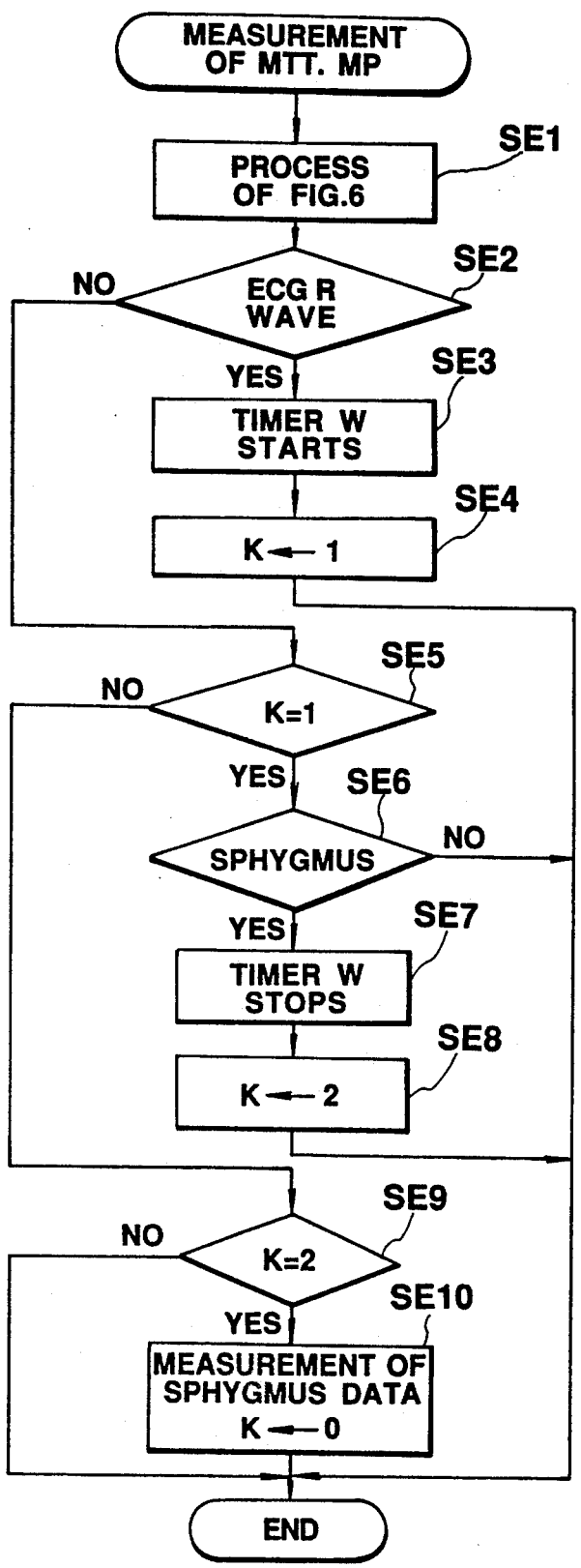
FIG. 19 is a flowchart showing an MTT/MP process of FIG. 18 in detail.

At step SE1 of FIG. 19, the control section 14 performs the process of the flowchart of FIG. 6 except the calculation process of sphygmus at step A6. More particularly, at step SE1, the respective amplifier-gain of ECG wave detecting section 15a and the sphygmus detecting section 15b is controlled for performing pertinent detecting process. When the respective amplifier-gain of ECG wave detecting section 15a and the sphygmus detecting section 15b has been set properly, the operation goes to step SE2, where it is judged if ECG wave (electrocardiographic R wave) has been detected. When it is judged that no ECG wave has been detected, the operation goes to step SE5, where it is judged that N=1 is not true and further advances to step SE9, where it is judged that N=2 is not true and then the process is finished. When it is judged that no ECG wave has been detected, processes at steps SE5 and SE9 are repeated until ECG wave is detected. When it is judged at step SE2 that ECG wave has been detected, the operation goes to step SE3, where the register W (not shown) of RAM 119 is caused to start time-counting operation, and further advances to step SE4, where a value "1" is set to the flag register K (not shown), and then returns to the original routine process.

As described above, when ECG wave has been detected, the timer W starts its operation.

When once the flag register k has been set to a value "1", the operation advances from step SE2 to SE5, where it is judged if K=1 is true. Then, the operation goes to step SE6, as it is judged at step SE5 that K=1 is true. At step SE6, it is judged if sphygmus has been detected after detection of ECG wave. When sphygmus has been detected, the timer register W is caused to stop its operation at step SE7. At step SE8, the flag register K is set to a value "2" and the operation goes back to the original routine operation.

As described above, when sphygmus has been detected, the timer register W is caused to stop its operation and the flag register K is set to a value "2". That is, time interval between the time when ECG wave is detected and the time when sphygmus is detected in a finger tip of the subject, i.e., sphygmus transmission rate shown as a time interval "T" in FIG. 7, is stored in the timer register W.

When it is judged at step SE5 that K=1 is not true, the operation goes to step SE9, where it is judged if K=2 is true. When K=2 is true, the operation goes to step SE10, where two successive sphygmus are detected to measure a time interval between them, and sphygmus data is obtained from the measured time interval. The time interval data of the timer register W obtained from ECG wave measured at step SE2 and sphygmus measured at step SE6 is stored as sphygmus transmission rate in the register MTT of RAM 119. Further, the above sphygmus data is stored in the register MP of RAM 119 and a value "1" is set to the register K, completing the present process.

As described above, sphygmus transmission rate data and sphygmus data are measured and these measured data are stored in the registers MTT, MP of RAM 119, respectively.

Bio Measurement and Display/Alarm

Now, referring to FIG. 18 again, the bio measurement and display/alarm operation in the bio feed-back mode will be described. The bio measurement of the present embodiment can be effectively used to train a subject for reducing his blood pressure and sphygmus, by making himself easy and relaxed while blood pressure and sphygmus are being measured.

When it is judged at step SD1 in FIG. 18 that M=1 is not true, the operation goes to step SD12, where it is judged if M=2 and F=2 are true. When it is judged that M=2 and F=2 are true, it is judged that the bio measurement display mode of the bio feed-back mode has been set. Then the operation goes to step SD13, where a value "1" is added to the register C (timer C). At step SD14, it is judged if the register C has been set to "10 sec". If not, the operation goes back to step SD12 and repeats the processes at steps SD12, SD13 and SD14 until the register C is set to "10 sec". When it is judged that the register C has been set to "10 sec", the operation goes to step SD15, where the measurement process of MTT and MP is performed. In the measurement process of MTT and MP, the highest blood pressure data and the lowest blood pressure data are calculated from time interval data and sphygmus data stored in the registers MTT, MP respectively and set values (four constants) set in the registers L0, L1, and are stored in the registers MS, MD, respectively. While the highest blood pressure data, the lowest blood pressure data and sphygmus data are stored in the register sections KS, KD and KP of the register Kj designated by an address pointer P of RAM 119, respectively.

As described above, blood pressure data are detected every "10 sec" in the bio measurement display mode, when the subject sets his right finger tip to the ECG wave detecting section 15a and the sphygmus detecting section 15b. The highest blood pressure data, the lowest blood pressure data and sphygmus data are calculated from the detected blood pressure data, and the data thus calculated are stored in the register sections KS, KD and KP of the register Kj of RAM 119.

Following the process at step SD15, the operation goes to step SD16, where data selected in the bio selection mode from the above calculated highest blood pressure data, lowest blood pressure data and sphygmus data is compared with the target data which has been set in the bio setting mode. When a substantial coincidence between the data has been detected at step SD16, the operation goes to step SD17, where the sounding section 16 is caused to make an acoustic alarm. When no coincidence between the data has been detected at step SD16, the operation returns to step SD18.

As described above, the data measured every 10 sec in the bio measurement mode is compared with the data set5 in the bio setting mode, and the acoustic alarm is output when both the data coincide with each other.

Note that if both the data to compared with each other fall within a predetermined range, it is judged that both the data coincide with each other in the present embodiment. For instance, in case that a value "125" is set as the highest blood pressure, the measured blood pressure ranging from "123" to "127" is judged to be coincident with the data set previously. Note that, when the measured blood pressure is not higher than the blood pressure set as the target value, an acoustic alarm may be output, because the subject would make use of the embodiment to reduce his blood pressure.

Now, the operation goes to step SD18, where the address pointer P is renewed to set an address of the register Ki (i=j+1) for storing the following measured data, and then further goes to step SD19, where it is judged if the bio measurement is final, i.e., if the address pointer P indicates that all of the register Kj involved in RAM 119 have been used. When the bio measurement is not final, the operation returns to the main flow of FIG. 17. The control section 14 performs the display process at step SC5 and repeats the process of FIG. 18. When it is judged at step SD19 that the bio measurement is final, the operation goes to step SD20, where a value "0" is set to the register G and the blood pressure measurement is finished, and then the operation returns to the main flow.

As described above, the registers Kj are successively designated every 10 sec, i.e., every time the bio measurement is performed, before the measurement is completed, and measured data are successively stored in the designated register Kj and are displayed on LCD2.

In the display process of the bio measurement, the data to be selected and set, i.e., the target value "125" of the highest blood pressure is displayed in a blinking manner, as shown at MD33 in FIG. 16, and the data measured every 10 sec is compared with the target value of the highest blood pressure. The result of the comparison is displayed on the dot matrix display section 102A. The dot matrix display section is divided into five display sections and one of the five display sections is turned on to indicate a result of the measurement. For example, when a measured data is considerably higher than the target value, the display section 133 at the highest position is turned on as shown at MD33 of FIG. 16. When a measured data is slightly higher than the target value, the display section 134 at the second highest position is turned on as shown at MD33 of FIG. 16 and when a measured data is substantially equivalent to the target value, the display section 135 at the middle position is turned on as shown at MD33 of FIG. 16. In a similar manner, when a measured data is considerably lower than the target value, the display section at the lowest position is turned on and when a measured data is slightly lower than the target value, the display section 134 at the second lowest position is turned on. The dot matrix display section shows as described above, so that the subject is allowed to confirm the result of comparison of every data with the target value at first sight. Meanwhile, the result of comparison of every data with the target value may be displayed in a lateral direction, which allows the subject to confirm an effect of the bio feed back every 10 sec.

In the present embodiment, the bio measurement is simply performed with respect to the highest blood pressure, the lowest blood pressure and sphygmus while the subject wears the wrist watch on his wrist and puts his finger tips on the recesses on the front surface of the wrist watch, i.e., on the ECG wave detecting section and the sphygmus detecting section of the wrist watch. As described above, there is no need to use a large case instrument which is complex in handling, but the subject can carry with him the wrist watch according to the present embodiment and is allowed to perform the bio measurement at any place and at any time he likes. In addition, he receives no pressure on his body such as on finger tips during measurement, so that he can keep calm and is allowed to concentrate his mind and to keep mental ease.

In the above embodiment, the result of comparison of the measured data with the target value is displayed on LCD 102 every bio measurement, but all of the data stored in RAM 119 may be displayed on LCD 102 at the same time, when the bio measurement is finished.

Further, the embodiment has been described which is applied to an electronic wrist watch but the device itself may be a haemadynamometer, provided with no watch function, of a wrist watch type. The device according to the embodiments of the present invention may be combined with an electronic note book or an electronic scheduler and various modifications and changes thereof may be apparent to those skilled in the art. A combination of LED and a photo transistor is used for detecting sphygmus in the embodiments but other pressure sensors may be employed. Further, there are provided registers L0, L1 in the embodiments for storing constants that are calculated from input highest blood pressure, lowest blood pressure, and measured sphygmus data and time interval data, but, without storing the constants in the registers L0, L1, blood pressure may be calculated every time measurement is performed.

Display of blood pressure data and sphygmus data stored in the registers Kj has not been described, but these data may be sequentially displayed on LCD 102 every time another switch S6 is operated.

Third Embodiment

In the second embodiment described above, blood pressure in blood vessel is not measured but blood pressure is calculated from sphygmus and sphygmus transmission rate. In the bio measurement, pressure in blood vessel may be actually measured.

Figure 20:
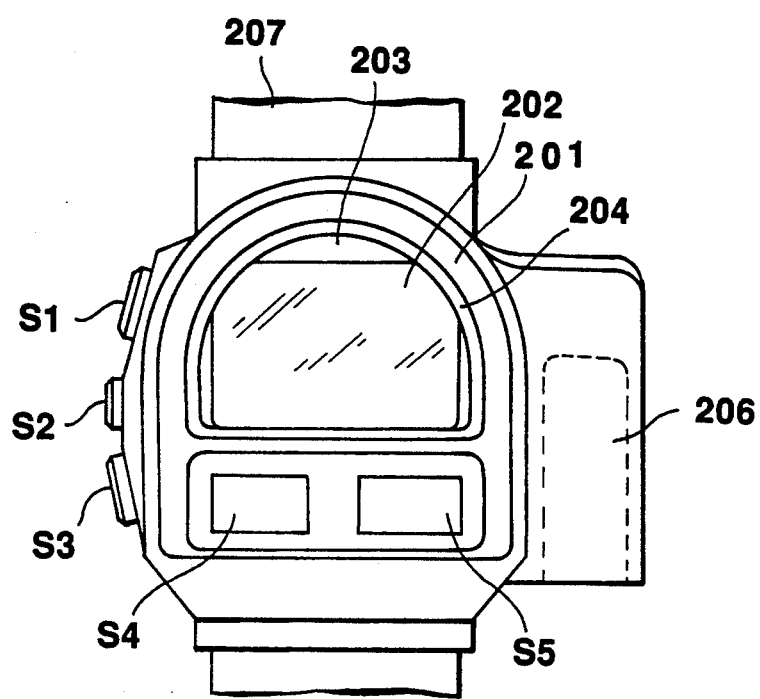
FIG. 20 is a view showing an external view of an electronic wrist watch employing the third embodiment of the present invention.

FIG. 20 is a view showing an external appearance of a wrist watch for measuring pressure in a blood vessel.

In FIG. 20, a watch casing 201 is provided with LCD 202 covered with a watch glass 203. The watch glass 203 is fixed on the watch casing 201 by packing member 204. On the left side wall (as viewed in FIG. 20) there are provided push button switches S1 to S3 and further below LCD 202 there are provided other switches S4, S5.

The watch casing 201 is formed with a hole 206 in its right side portion (as viewed in FIG. 20). The hole 206 receives a finger of a human. In the hole 206 is mounted a haemadynamometer system (not shown) comprising an elastic tube, pressure pump room and an optical sensor for measuring blood pressure in blood vessel in the finger tip inserted into the hole 206.

The watch casing 201 is further provided with strips 207 for being worn on a wrist of a human.

The wrist watch of FIG. 20 is allowed to perform the bio feed back measurement with a finger tip inserted into the hole 206.

Fourth Embodiment

In the second embodiment described above, only the present time is displayed in the watch mode of M=0 as shown in FIG. 16, but the lowest blood pressure and the highest blood pressure stored in the registers Kj may be displayed on the dot matrix display section 102A by operation of the switches S3, S4.

Figure 21:
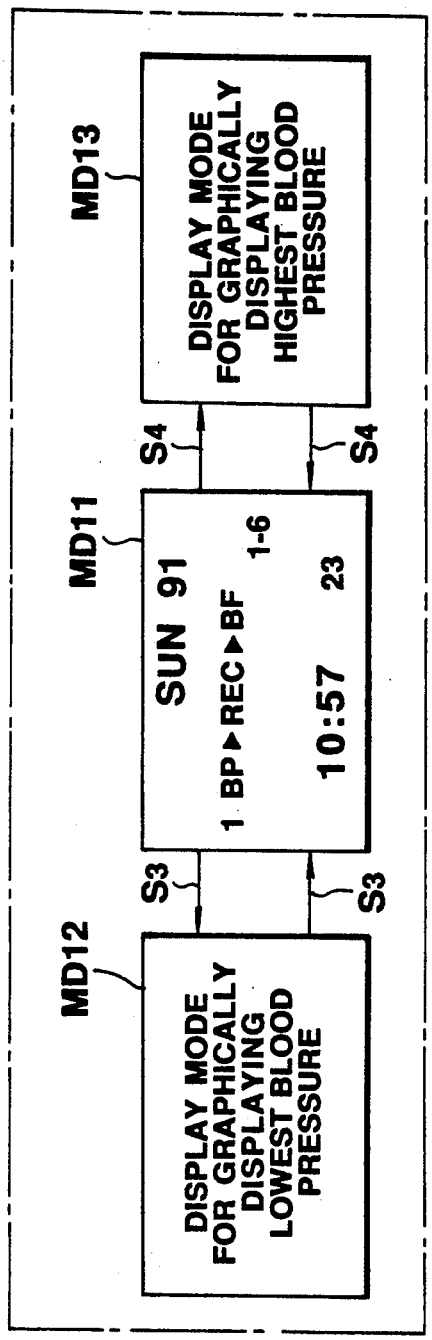
FIG. 21 is a view showing displays in the fourth embodiment of the present invention.

More particularly, when the switch S3 is operated while the present time is displayed as shown at MD11 of FIG. 21, a lowest blood pressure display mode of MD12 is selected to graphically display lowest blood pressure and when the switch S4 is operated while the present time is displayed as shown at MD11 of FIG. 21, a highest blood pressure display mode of MD13 is selected to graphically display highest blood pressure.

Figure 22A:
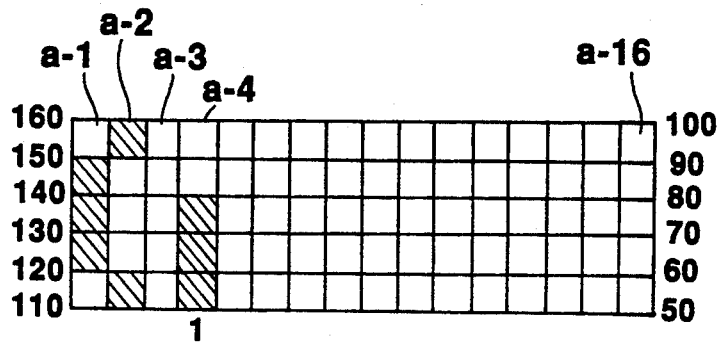
FIGS. 22A through 22H are views showing display states of FIG. 21 in detail.
Figure 22B:
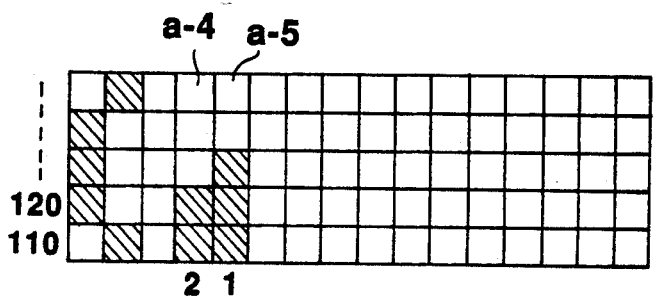
Figure 22C:
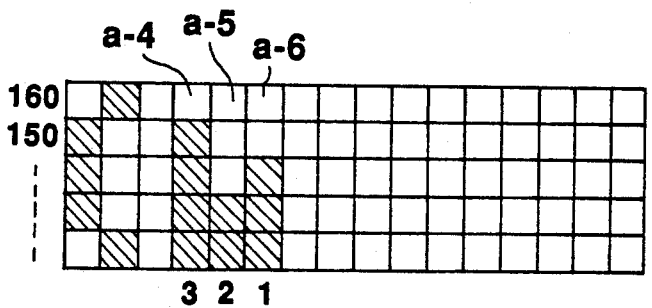
Figure 22D:
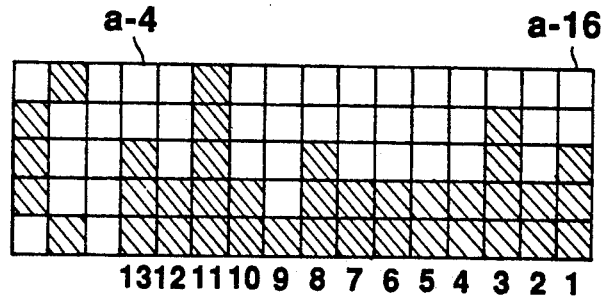

FIGS. 22A through 22D are views showing that highest blood pressures are graphically displayed in the graphically displaying mode. In FIG. 22A, numerals left to the dot matrix display section 102A represent values of highest blood pressure. The dot matrix display section 102A comprises 16 sets of lateral display sections, a-1, a-2 through a-16. Each lateral display section involves 5 dots. The turned-on dots involved in the left lateral display section a-1 and the second lateral display section a-2 from the left end show that the display indicates highest blood pressure, referring to the numerals printed on the left side of the display section 102A. A value of actual blood pressure is shown by the remaining lateral display sections a-4 through a-16 except the lateral display section a-3. In FIG. 22A, three dots are turned on, showing that the first highest blood pressure falls within the range of "130 to 139". FIG. 22B is a view showing the indication, which is turned on after a predetermined time lapse, for example one sec. later, from the indication of FIG. 22A. In FIG. 22B, three turned-on dots moves to the fifth lateral display section a-5 and two other dots in the fourth lateral display section a-4 are turned on, showing that the following highest blood pressure falls within the range of "120 to 129". FIG. 22C is a view showing the indication, which is turned on after another one sec. In FIG. 22C, the three turned-on dots and the two turned-on dots are shifted to the right by one lateral display section, respectively and four other dots in the fourth lateral display section a-4 are turned on, showing that the highest blood pressure falls within the range of "140 to 149". FIG. 22D is a view showing that measured highest blood pressure are sequentially indicated. The blood pressure measured for the first time is now indicated by the lateral display section a-16 while the latest blood pressure is indicated by the lateral display section a-4.

Figure 22E:
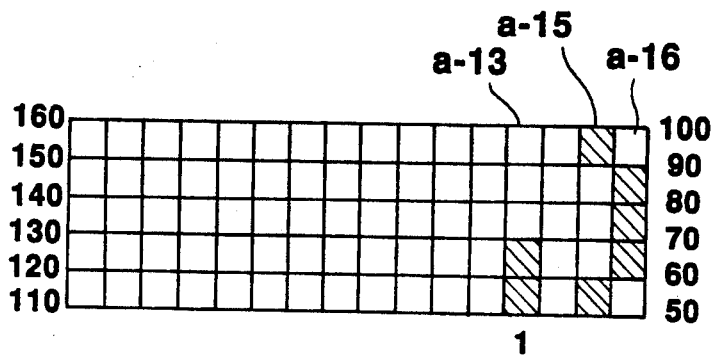
Figure 22F:
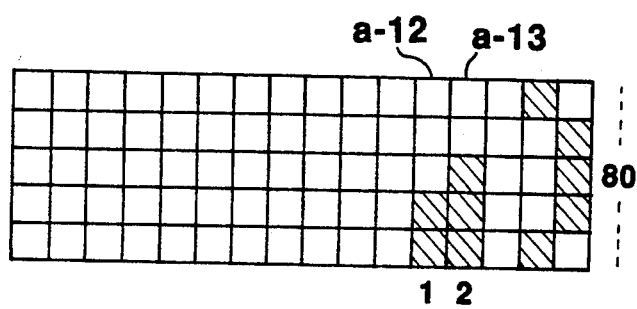
Figure 22G:
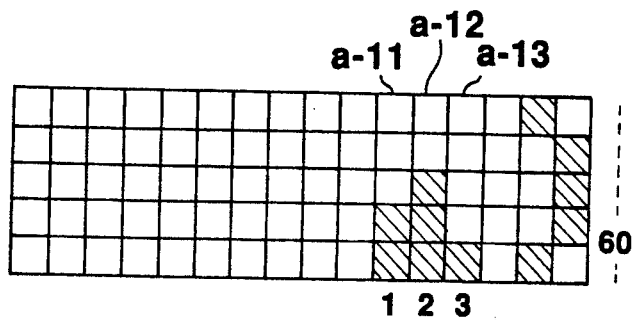
Figure 22H:
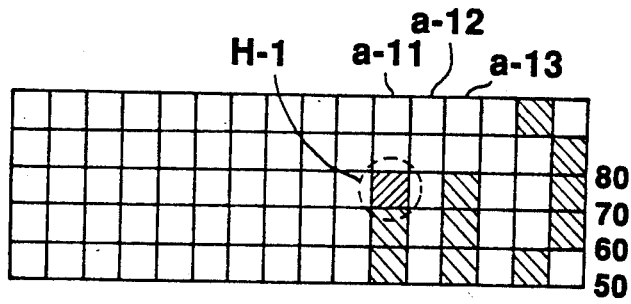

As described above, stored highest blood pressure are sequentially indicated and the latest blood pressure is indicated, for convenience, by the lateral display section close to the numerals printed left to the display section 102A. FIGS. 22E through 22H are views showing that lowest blood pressures are graphically displayed in the graphically displaying mode. In FIG. 22A, numerals right to the dot matrix display section 102A represent values of lowest blood pressure. Contrary to the indication of the highest blood pressure, two lateral display sections a-16, a-15 show that the indication represents lowest blood pressure, referring to the numerals printed on the right to the display section 102A. The first lowest blood pressure is indicated by the lateral display section a-13. In FIG. 22E, two dots in the lateral display section a-13 are turned on, showing that the first lowest blood pressure falls within the range of "60 to 70". FIG. 22F is a view showing the indication turned on after one second from the first indication of FIG. 22E. The two turn-on dots move to the left to the lateral display section a-12 and three other dots involved in the lateral display section a-13 are turned on, showing that the lowest blood pressure measured for the second time falls within the range of "70 to 80". FIG. 22G is a view showing that the indications of the first and second blood pressure are moved to the left by one lateral display section, respectively. The first blood pressure and second blood pressure are indicated by the lateral display sections a-11, a-12, respectively and the third blood pressure is now indicated by one turn-on dot involved in the lateral display section a-13.

As described above, the lowest blood pressure are sequentially displayed by the lateral display sections in order of the measurement and the latest blood pressure is displayed, for convenience, by the lateral display section a-113 closest to the numerals printed on the right to the display section 102A. Similarly to the indication of highest blood pressure, 13 data of lowest blood pressure are graphically indicated so that changes in lowest blood pressure are recognized for first sight.

The highest blood pressure and the lowest blood pressure are indicated by the same display member in the above embodiment, so that a device involving the embodiment is allowed to be made compact in size.

In the above embodiment, blood pressure are successively indicated every one second but blood pressure may be successively indicated by every operation on an external switch. Level of blood pressure is indicated by dots each representative of 10 unit but blood pressure may be indicated by a top dot H-1 of FIG. 22H, which is turned on in a blinking manner, showing a level of "0 to 4" or by the top dot H-1, which is turned on stationary, showing a level of "5 to 9".

What is claimed is:

1. A device for measuring an electrocardiographic wave and sphygmus, comprising:
   electrocardiographic wave detecting means for detecting an electrocardiographic wave in a human body to generate an electric signal;
   first amplifying means for amplifying said electric signal received from said electrocardiographic wave detecting means to generate an electrocardiographic wave signal;
   first gain data storing means for storing first gain data to control the gain of said first amplifying means;
   sphygmus detecting means for detecting sphygmus in a blood vessel to generate an electric signal;
   second amplifying means for amplifying the electric signal received from said sphygmus detecting means to generate a sphygmus signal;
   second gain data storing means for storing second gain data to control the gain of said second amplifying means;
   judging means for determining whether the electrocardiographic wave signal generated by said first amplifying means and the sphygmus signal generated by said second amplifying means are in correspondence with each other; and
   gain control means for changing one of said first and second gain data to control the gain of its associated amplifying means when said judging means determines that said electrocardiographic wave signal and said sphygmus signal are not in correspondence with each other.

2. A device according to claim 1, further comprising:
   calculation means for calculating the number of sphygmus in a predetermined time period from said electrocardiographic wave signal or said sphygmus signal; and
   display means for displaying the number of sphygmus in said predetermined time period calculated by said calculation means.

3. A device according to claim 1, further comprising:
   first time measuring means for measuring a time interval between two successive electrocardiographic wave signals;
   second time measuring means for measuring a time interval between two successive sphygmus signals;
   calculation means for calculating the number of sphygmus in a predetermined time period, when the time interval measured by said first time measuring means is substantially equivalent to the time interval measured by said second time measuring means; and
   display means for displaying the number of sphygmus in said predetermined time period calculated by said calculation means.

4. A device according to claim 1, further comprising:
   time measuring means for measuring a time interval between a time when said electrocardiographic wave detecting means has detected the electrocardiographic wave and a time when said sphygmus detecting means has detected the sphygmus to obtain time data;
   calculation means for calculating blood pressure data using the time data obtained by said time measuring means; and
   display means for displaying the blood pressure data calculated by said calculation means.

5. A device according to claim 4, wherein said calculation means calculates highest blood pressure data and lowest blood pressure data.

6. A device according to claim 1, wherein said sphygmus detecting means comprises light emitting means for emitting light, and light receiving means for receiving the light emitted from said light emitting means.

7. A device for measuring an electrocardiographic wave and sphygmus, comprising:
   electrocardiographic wave detecting means for detecting an electrocardiographic wave in a human body to generate an electric signal;
   first amplifying means for amplifying said electric signal received from said electrocardiographic -wave detecting means to generate electrocardiographic wave signals;
   sphygmus detecting means for detecting sphygmus in a blood vessel to generate an electric signal;

second amplifying means for amplifying the electric signal received from said sphygmus detecting means to generate sphygmus signals;

judging means for determining whether any one of the electrocardiographic wave signals generated by said first amplifying means and the sphygmus signals generated by said second amplifying means has been outputted following the other signal; and gain control means for increasing the gain of one of said first and second amplifying means which outputs the signal that has not been outputted following the other signal, when said judging means determines that one of the electrocardiographic wave signals generated by said first amplifying means and the sphygmus signals generated by said second amplifying means has not been outputted following the other signal.

8. A device according to claim 7, further comprising:

calculation means for calculating the number of sphygmus in a predetermined time period from one of the electrocardiographic wave signals and the sphygmus signals; and display means for displaying the number of sphygmus in the predetermined time period calculated by said calculation means.

9. A device according to claim 7, further comprising:

first time measuring means for measuring a time interval between two successive ones of said electrocardiographic wave signals;

second time measuring means for measuring a time interval between two successive ones of said sphygmus signals;

calculation means for calculating the number of sphygmus in a predetermined time period when the time interval measured by said first time measuring means is substantially equivalent to the time interval measured by said second time measuring means; and display means for displaying the number of sphygmus in the predetermined time period calculated by said calculation means.

10. A device according to claim 7, further comprising:

time measuring means for measuring a time interval between a time when said electrocardiographic wave detecting means has detected the electrocardiographic wave and a time when said sphygmus detecting means has detected the sphygmus to obtain time data;

calculation means for calculating blood pressure data using the time data obtained by said time measuring means; and display means for displaying the blood pressure data calculated by said calculation means.

11. A device according to claim 10, wherein said calculation means calculates highest blood pressure data and lowest blood pressure data.

12. A device according to claim 7, wherein said sphygmus detecting means comprises light emitting means for emitting light, and light receiving means for receiving the light emitted from said light emitting means.

13. A device for measuring an electrocardiographic wave and sphygmus, comprising:

electrocardiographic wave detecting means for detecting an electrocardiographic wave in a human body to generate an electric signal;

first amplifying means for amplifying the electric signal received from said electrocardiographic wave detecting means to generate an electrocardiographic wave signal;

electrocardiographic-wave time measuring means for measuring a time interval between two successive electrocardiographic wave signals generated by said first amplifying means;

first judging means for determining whether the time interval measured by said electrocardiographic-wave time measuring means falls within a predetermined time range;

first gain control means for changing the gain of said first amplifying means when said first judging means determines that the time interval measured by said electrocardiographic-wave time measuring means does not fall within the predetermined time range;

sphygmus detecting means for detecting sphygmus in a blood vessel to generate an electric signal;

second amplifying means for amplifying the electric signal received from said sphygmus detecting means to generate a sphygmus signal;

sphygmus time measuring means for measuring a time interval between two successive sphygmus signals generated by said second amplifying means;

second judging means for determining whether the time interval measured by said sphygmus time measuring means falls within a predetermined time range;

second gain control means for changing the gain of said second amplifying means when said second judging means determines that the time interval measured by said sphygmus time measuring means does not fall within the predetermined time range;

third judging means for determining whether the electrocardiographic wave signal generated by said first amplifying means and the sphygmus signal generated by said second amplifying means are in correspondence with each other; and third gain control means for controlling the gain of one of said first amplifying means and of said second amplifying means when said third judging means determines that said electrocardiographic wave signal and said sphygmus signal are not in correspondence with each other.

14. A device according to claim 13, further comprising:

calculation means for calculating the number of sphygmus in a predetermined time period from one of the electrocardiographic wave signal and the sphygmus signal; and display means for displaying the number of sphygmus in the predetermined time period calculated by said calculation means.

15. A device according to claim 13, further comprising:

first time measuring means for measuring a time interval between two successive electrocardiographic wave signals;

second time measuring means for measuring a time interval between two successive sphygmus signals;

calculation means for calculating the number of sphygmus in a predetermined time period when the time interval measured by said first time measuring means is substantially equivalent to the time interval measured by said second time measuring means; and display means for displaying the number of sphygmus in the predetermined time period calculated by said calculation means.

16. A device according to claim 13, further comprising:
    time measuring means for measuring a time interval between a time when said electrocardiographic wave detecting means has detected the electrocardiographic wave and a time when said sphygmus detecting means has detected the sphygmus to obtain time data;
    calculation means for calculating blood pressure data using the time data obtained by said time measuring means; and
    display means for displaying the blood pressure data calculated by said calculation means.

17. A device according to claim 16, wherein said calculation means calculates highest blood pressure data and lowest blood pressure data.

18. A device according to claim 13, wherein said sphygmus detecting means comprises light emitting means for emitting light, and light receiving means for receiving the light emitted by said light emitting means.

19. A device for measuring blood-pressure data, comprising:
    blood-pressure data input means for inputting blood-pressure data;
    blood-pressure data storing means for storing the blood-pressure data inputted by said blood-pressure data input means;
    blood-pressure detecting means for detecting blood pressure at predetermined intervals to generate blood-pressure data;
    comparison means for comparing the blood-pressure data, detected every time when said blood-pressure detecting means detects blood pressure, with the blood-pressure data stored in said blood-pressure data storing means; and
    alarm means for producing an alarm as a result of the comparison made by said comparison means to indicate whether the detected blood-pressure data is higher than the stored blood-pressure data;
    a plurality of detected blood-pressure data storing means for storing the blood-pressure data which are detected by said blood-pressure detecting means at a predetermined interval; and
    stop means for causing said blood-pressure detecting means to stop measuring blood pressure when all of the plurality of detected blood-pressure data storing means store blood-pressure data.

20. A device according to claim 19, wherein said blood-pressure detecting means comprises:
    sphygmus detecting means for detecting sphygmus;
    electrocardiographic wave detecting means for detecting an electrocardiographic wave;
    time measuring means for measuring a time interval between a time when said sphygmus detecting means detects a sphygmus and a time when said electrocardiographic wave detecting means detects an electrocardiographic wave, to generate time data; and
    calculation means for calculating blood-pressure data from the time data generated by said time measuring means.

21. A device according to claim 19, wherein said blood-pressure detecting means detects highest blood-pressure data and lowest blood-pressure data.

22. A device according to claim 19, wherein said blood-pressure data inputting means comprises input means for inputting a highest blood-pressure data and input means for inputting a lowest blood-pressure data.

23. A device according to claim 19, wherein said blood-pressure data storing means has a memory area for storing a highest blood-pressure data and a memory area for storing a lowest blood-pressure data.

24. A device for measuring blood-pressure data, comprising:
    blood-pressure data input means for inputting blood-pressure data;
    blood-pressure data storing means for storing the blood-pressure data inputted by said blood-pressure data input means;
    blood-pressure detecting means for detecting blood pressure at a predetermined interval to generate blood-pressure data;
    comparison means for comparing the blood-pressure data, detected every time when said blood-pressure detecting means detects blood pressure, with the blood-pressure data stored in said blood-pressure data storing means; and
    alarm means for producing an alarm as a result of the comparison made by said comparison means to indicate whether the detected blood-pressure data is higher than the stored blood-pressure data;
    a plurality of detected blood-pressure data storing means for storing the blood-pressure data which are detected by said blood-pressure detecting means at a predetermined interval; and
    display means for displaying the blood-pressure data stored in said plurality of detected blood-pressure data storing means.

25. A device according to claim 24, wherein said blood-pressure detecting means comprises:
    sphygmus detecting means for detecting sphygmus;
    electrocardiographic wave detecting means for detecting an electrocardiographic wave;
    time measuring means for measuring a time interval between a time when said sphygmus detecting means detects a sphygmus and a time when said electrocardiographic wave detecting means detects an electrocardiographic wave, to generate time data; and
    calculation means for calculating blood-pressure data from the time data generated by said time measuring means.

26. A device according to claim 24, wherein said blood-pressure detecting means detects highest blood-pressure data and lowest blood-pressure data.

27. A device according to claim 24, wherein said blood-pressure data inputting means comprises input means for inputting a highest blood-pressure data and input means for inputting a lowest blood-pressure data.

28. A device according to claim 24, wherein said blood-pressure data storing means has a memory area for storing a highest blood-pressure data and a memory area for storing a lowest blood-pressure data.

* * * * *